US008696589B2

(12) United States Patent
Kwok et al.

(10) Patent No.: US 8,696,589 B2
(45) Date of Patent: Apr. 15, 2014

(54) METHOD AND SYSTEM FOR HEART FAILURE STATUS EVALUATION BASED ON A DISORDERED BREATHING INDEX

(75) Inventors: Jonathan T. Kwok, Holmdel, NJ (US); Marina Brockway, Shoreview, MN (US); Kent Lee, Shoreview, MN (US); Quan Ni, Shoreview, MN (US); Yachuan Pu, San Diego, CA (US); Jeffrey E. Stahmann, Ramsey, MN (US); Yi Zhang, Plymouth, MN (US); Jesse W. Hartley, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 502 days.

(21) Appl. No.: 12/847,698

(22) Filed: Jul. 30, 2010

(65) Prior Publication Data
US 2010/0298733 A1 Nov. 25, 2010

Related U.S. Application Data

(62) Division of application No. 11/291,525, filed on Dec. 1, 2005, now Pat. No. 7,766,840.

(51) Int. Cl.
*A61B 5/08* (2006.01)
(52) U.S. Cl.
USPC ............................ 600/529; 600/532; 600/538
(58) Field of Classification Search
USPC .................................................. 600/529–543
See application file for complete search history.

(56) References Cited

U.S. PATENT DOCUMENTS

| 4,697,591 | A | 10/1987 | Lekholm et al. |
| 5,063,927 | A | 11/1991 | Webb et al. |
| 5,133,353 | A | 7/1992 | Hauser |
| 5,179,945 | A | 1/1993 | Van Hofwegen et al. |
| 5,314,459 | A | 5/1994 | Swanson et al. |
| 5,318,597 | A | 6/1994 | Hauck et al. |
| 5,372,606 | A | 12/1994 | Lang et al. |
| 5,411,525 | A | 5/1995 | Swanson et al. |
| 5,468,254 | A | 11/1995 | Hahn et al. |

(Continued)

FOREIGN PATENT DOCUMENTS

| EP | 1151719 | 7/2001 |
| EP | 1177764 | 6/2002 |

(Continued)

OTHER PUBLICATIONS

File History for EP Application No. 06838547.5 as retrieved from European Patent Office System on Oct. 1, 2012, 85 pages.

(Continued)

*Primary Examiner* — Michael Kahelin
*Assistant Examiner* — Karen Toth
(74) *Attorney, Agent, or Firm* — Seager, Tufte & Wickhem LLC

(57) ABSTRACT

An evaluation of heart failure status is provided based on a disordered breathing index. Patient respiration is sensed and a respiration signal is generated. Disordered breathing episodes are detected based on the respiration signal. A disordered breathing index is determined based on the disordered breathing episodes. The disordered breathing index is trended and used to evaluate heart failure status. The disordered breathing index may be combined with additional information and/or may take into account patient activity, posture, sleep stage, or other patient information.

8 Claims, 18 Drawing Sheets

(56) References Cited

U.S. PATENT DOCUMENTS

| | | | |
|---|---|---|---|
| 5,593,431 | A | 1/1997 | Sheldon |
| 5,620,466 | A | 4/1997 | Haefner et al. |
| 5,634,938 | A | 6/1997 | Swanson et al. |
| 5,662,688 | A | 9/1997 | Haefner et al. |
| 5,697,953 | A | 12/1997 | Kroll et al. |
| 5,957,861 | A | 9/1999 | Combs et al. |
| 5,974,349 | A | 10/1999 | Levine |
| 6,044,297 | A | 3/2000 | Sheldon et al. |
| 6,275,727 | B1 | 8/2001 | Hopper et al. |
| 6,360,127 | B1 | 3/2002 | Ding et al. |
| 6,409,675 | B1 | 6/2002 | Turcott |
| 6,438,407 | B1 | 8/2002 | Ousdigian et al. |
| 6,449,509 | B1 | 9/2002 | Park et al. |
| 6,454,719 | B1 | 9/2002 | Greenhut |
| 6,513,532 | B2 | 2/2003 | Mault et al. |
| 6,527,729 | B1 | 3/2003 | Turcott |
| 6,564,106 | B2 | 5/2003 | Guck et al. |
| 6,572,557 | B2 | 6/2003 | Tchou et al. |
| 6,658,292 | B2 | 12/2003 | Kroll et al. |
| 6,666,826 | B2 | 12/2003 | Salo et al. |
| 6,705,990 | B1 | 3/2004 | Gallant et al. |
| 6,708,058 | B2 | 3/2004 | Kim et al. |
| 6,741,885 | B1 | 5/2004 | Park et al. |
| 6,752,765 | B1 | 6/2004 | Jensen et al. |
| 6,832,113 | B2 | 12/2004 | Belalcazar |
| 6,856,829 | B2 | 2/2005 | Ohsaki et al. |
| 6,922,587 | B2 | 7/2005 | Weinberg |
| 6,993,389 | B2 | 1/2006 | Ding |
| 7,013,176 | B2 | 3/2006 | Ding |
| 7,020,521 | B1 | 3/2006 | Brewer et al. |
| 7,041,061 | B2 | 5/2006 | Kramer |
| 7,115,096 | B2 | 10/2006 | Siejko |
| 7,158,830 | B2 | 1/2007 | Yu |
| 7,181,285 | B2 | 2/2007 | Lindh |
| 7,206,634 | B2 | 4/2007 | Ding |
| 7,228,174 | B2 | 6/2007 | Burnes |
| 7,306,564 | B2 | 12/2007 | Nakatani et al. |
| 7,310,554 | B2 | 12/2007 | Kramer |
| 7,343,199 | B2 | 3/2008 | Hatlestad |
| 7,376,457 | B2 | 5/2008 | Ross |
| 7,389,141 | B2 | 6/2008 | Hall |
| 7,409,244 | B2 | 8/2008 | Salo |
| 7,468,032 | B2 | 12/2008 | Stahmann et al. |
| 7,483,743 | B2 | 1/2009 | Mann et al. |
| 7,572,225 | B2 | 8/2009 | Stahmann et al. |
| 7,766,840 | B2 * | 8/2010 | Kwok et al. ............... 600/508 |
| 8,192,376 | B2 | 6/2012 | Lovett et al. |
| 8,200,336 | B2 * | 6/2012 | Tehrani et al. ............ 607/42 |
| 2001/0037067 | A1 | 11/2001 | Tchou et al. |
| 2001/0049470 | A1 | 12/2001 | Mault et al. |
| 2002/0143264 | A1 | 10/2002 | Ding et al. |
| 2002/0193697 | A1 | 12/2002 | Cho et al. |
| 2003/0055461 | A1 | 3/2003 | Girouard et al. |
| 2003/0078619 | A1 | 4/2003 | Bonnet et al. |
| 2004/0019289 | A1 | 1/2004 | Ross |
| 2004/0116819 | A1 | 6/2004 | Alt |
| 2004/0122294 | A1 | 6/2004 | Hatlestad et al. |
| 2004/0127792 | A1 | 7/2004 | Siejko |
| 2004/0133079 | A1 | 7/2004 | Mazar et al. |
| 2004/0242997 | A1* | 12/2004 | Griffin et al. ............. 600/437 |
| 2005/0085738 | A1* | 4/2005 | Stahmann et al. .......... 600/529 |
| 2005/0113711 | A1 | 5/2005 | Nakatani et al. |
| 2005/0137629 | A1 | 6/2005 | Dyjach et al. |
| 2006/0135878 | A1* | 6/2006 | Wright et al. ............. 600/538 |
| 2007/0055115 | A1 | 3/2007 | Kwok et al. |
| 2007/0073168 | A1 | 3/2007 | Zhang et al. |
| 2007/0118183 | A1* | 5/2007 | Gelfand et al. ............ 607/42 |
| 2007/0129643 | A1 | 6/2007 | Kwok et al. |
| 2007/0135725 | A1 | 6/2007 | Hatlestad |
| 2007/0179389 | A1 | 8/2007 | Waruar |
| 2007/0239057 | A1 | 10/2007 | Pu et al. |
| 2008/0262360 | A1 | 10/2008 | Dalal et al. |

FOREIGN PATENT DOCUMENTS

| | | |
|---|---|---|
| WO | WO9833553 | 6/1998 |
| WO | WO0240096 | 5/2002 |
| WO | WO03075744 | 9/2003 |
| WO | WO2004062485 | 7/2004 |
| WO | WO2005028029 | 3/2005 |
| WO | WO2008085309 | 7/2008 |

OTHER PUBLICATIONS

Maestri et al. "RESP-24: a computer program for the investigation of 24-h breathing abnormalities in heart failure patients" Computer Methods and Programs in Biomedicine, Elsevier, Amsterdam, NL, vol. 68. No. 2, May 1, 2002, pp. 147-159.

Office Action dated Jun. 14, 2011 for European Application No. 06838547.7, 6 pages.

Office Action dated Apr. 12, 2012 for Japanese Application No. 2008-543410 (partial translation), 1 page.

Altshule et al., "The Effect of Position on Periodic Breathing in Chronic Cardiac Decomposition", New Eng. Journal of Med., vol. 259, No. 22, pp. 1064-1066, Nov. 27, 1958.

Butler et al., "Beta-Blocker Use and Outcomes Among Hospitalized Heart Failure Patients", Journal of the American College of Cardiology, vol. 47, No. 12, 2006, pp. 2462-2469.

Dark et al., "Breathing Pattern Abnormalities and Arterial Oxygen Desaturation During Sleep in the Congestive Heart Failure Syndrome", Chest, Jun. 1987, 6:833-6. Abstract Only.

Dimopolou I, et al., "Pattern of Breathing during Progressive Exercise in Chronic Heart Failure", IJC 81 (2001), 117-121. Abstract Only.

Duguet et al., "Expiratory Flow Limitation as a Determinant of Orthopnea in Acute Left Heart Failure", Journal of the American College of Cardiology, vol. 35, No. 3, 2000, pp. 690-700.

Hoffman et al., "Cheyne-Stokes Respiration in Patients Recovering from Acute Cardiogenic Pulmonary Edema", Chest 1990, 97:410-12. Abstract Only.

Junyu et al., "Posture Detection Algorithm Using Multi Axis DC-Accelerometer", Pace vol. 22, Apr. 1999.

Lee et al., "Predicting Mortality Among Patients Hospitalized for Heart Failure, derivation and validation of a clinical model", JAMA, 2003, 290:2581-87. Abstract Only.

Rame et al., "Outcomes after emergency department discharge with a primary diagnosis of heart failure", American Heart Journal, vol. 142(4), Oct. 2001, pp. 714-719.

Rees et al., "Paroxysmal Nocturnal Dyspnoea and Periodic Respiration", The Lancet, Dec. 22-29, 1979, pp. 1315-1317. Abstract Only.

Solin et al., "Effects of Cardiac Dysfunction on Non-Hypercapnic Central Sleep Apnea", Department of Respiratory Medicine, Alfred Hospital, and Department of Medicine, Monash University Medical School, Melbourne, Victoria, Australia, Apr. 10, 1997, pp. 104-110.

Tkacova et al., "Left Ventricular Volume in Patients with Heart Failure and Cheyne-Strokes Respiration during Sleep", Am. Journal, Respir. Crit. Care Med., vol. 156, pp. 1549-1555, 1997.

Notice of Allowance dated Jun. 11, 2010 from U.S. Appl. No. 11/392,365, 4 pages.

Office Action Response dated May 14, 2010 from U.S. Appl. No. 11/392,365, 7 pages.

Interview Summary dated May 5, 2010 from U.S. Appl. No. 11/392,365, 3 pages.

Office Action dated Mar. 16, 2010 from U.S. Appl. No. 11/392,365, 8 pages.

Office Action Response dated Nov. 9, 2009 from U.S. Appl. No. 11/392,365, 8 pages.

Office Action Response dated May 26, 2009 from U.S. Appl. No. 11/392,365, 8 pages.

Interview Summary dated Apr. 29, 2009 from U.S. Appl. No. 11/392,365, 2 pages.

Office Action dated Jan. 26, 2009 from U.S. Appl. No. 11/392,365, 11 pages.

Office Action Response dated Nov. 20, 2008 from U.S. Appl. No. 11/392,365, 10 pages.

(56) References Cited

OTHER PUBLICATIONS

Office Action dated Oct. 20, 2008 from U.S. Appl. No. 11/392,365, 12 pages.
Notice of Allowance dated Jun. 15, 2010 from U.S. Appl. No. 11/291,525, 4 pages.
Notice of Allowance dated Mar. 23, 2010 from U.S. Appl. No. 11/291,525, 4 pages.
Office Action Response dated Mar. 5, 2010 from U.S. Appl. No. 11/291,525, 5 pages.
Office Action dated Dec. 8, 2009 from U.S. Appl. No. 11/291,525, 7 pages.
Office Action Response dated Sep. 11, 2009 from U.S. Appl. No. 11/291,525, 8 pages.
Office Action dated Jun. 24, 2009 from U.S. Appl. No. 11/291,525, 10 pages.
Office Action Response dated Mar. 17, 2009 from U.S. Appl. No. 11/291,525, 8 pages.
Interview Summary dated Mar. 9, 2009 from U.S. Appl. No. 11/291,525, 4 pages.
Office Action dated Nov. 28, 2008 from U.S. Appl. No. 11/291,525, 9 pages.
Office Action Response dated Oct. 22, 2008 from U.S. Appl. No. 11/291,525, 12 pages.
Office Action dated Sep. 23, 2008 from U.S. Appl. No. 11/291,525, 14 pages.
International Search Report and Written Opinion dated Mar. 21, 2007 from PCT Application No. PCT/US2006/045646, 13 pages.
International Preliminary Report on Patentability dated Jun. 12, 2008 from PCT Application No. PCT/US2006/045646, 8 pages.

\* cited by examiner

METHOD AND SYSTEM FOR HEART FAILURE STATUS EVALUATION BASED ON A DISORDERED BREATHING INDEX

RELATED PATENT DOCUMENT

This application is a division of U.S. patent application Ser. No. 11/291,525 filed on Dec. 1, 2005, to issue on Aug. 3, 2010 as U.S. Pat. No. 7,766,840 which is incorporated herein by reference.

FIELD OF THE INVENTION

The present invention relates generally to providing an evaluation of heart failure status based at least in part on a disordered breathing index.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiratory system, through the breathing mechanism, performs the function of exchanging these gases with the external environment. Together, the cardiac and respiratory systems form a larger anatomical and functional unit denoted the cardiopulmonary system.

Various disorders that affect the cardiovascular system may also impact respiration. For example, heart failure is an abnormality of cardiac function that causes cardiac output to fall below a level adequate to meet the metabolic demand of peripheral tissues. Heart failure (HF) is sometimes referred to as congestive heart failure due to the accompanying venous and pulmonary congestion. Congestive heart failure may have a variety of underlying causes, including ischemic heart disease (coronary artery disease), hypertension (high blood pressure), and diabetes, among others.

Various types of disordered respiration are associated with HF. For example, rapid shallow breathing is one of the cardinal signs of heart failure. The appearance of rapid, shallow breathing in a HF patient is often secondary to increased pulmonary edema, and can indicate a worsening of patient status. An abnormally high respiration rate thus can be an indicator of HF decompensation. It is estimated that nearly one million hospital admissions for acute decompensated congestive heart failure occur in the United States each year, which is almost double the number admitted 15 years ago. The re-hospitalization rates during the 6 months following discharge are as much at 50%. Nearly 2% of all hospital admissions in the United States are for decompensated HF patients, and heart failure is the most frequent cause of hospitalization in patients older than 65 years. The average duration of hospitalization is about 6 days. Despite aggressive therapies, hospital admissions for HF continue to increase, reflecting the prevalence of this malady.

Because of the complex interactions between the cardiovascular, pulmonary, and other physiological systems, as well as the need for early detection of various diseases and disorders, an effective approach to monitoring and early diagnosis is needed. Accurately characterizing patient respiration aids in monitoring and diagnosing respiration-related diseases or disorders. Evaluating patient respiration information may allow an early intervention, preventing serious decompensation and hospitalization.

SUMMARY OF THE INVENTION

An embodiment of the invention is directed to a method for operating a medical device to provide a patient assessment. Patient respiration is sensed and a respiration signal is generated. Disordered breathing episodes are detected based on the respiration signal. A disordered breathing index is determined based on the disordered breathing episodes. The disordered breathing index is trended and used to evaluate heart failure status. At least one of sensing patient respiration, detecting the disordered breathing episodes, determining the disordered breathing index, trending the index and evaluating the heart failure status is performed at least in part implantably.

Another embodiment of the invention involves a system for providing a patient assessment. A data acquisition module includes a respiration sensor and is configured to generate a signal responsive to patient respiration. A disordered breathing detector is coupled to the respiration sensor and is configured to detect disordered breathing episodes based on the respiration signal. An index processor determines a disordered breathing index based on the detected disordered breathing episodes. A trend/storage module is configured to develop and store a trend of the disordered breathing index. A diagnostics unit is configured to evaluate heart failure status based on the disordered breathing index trend.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
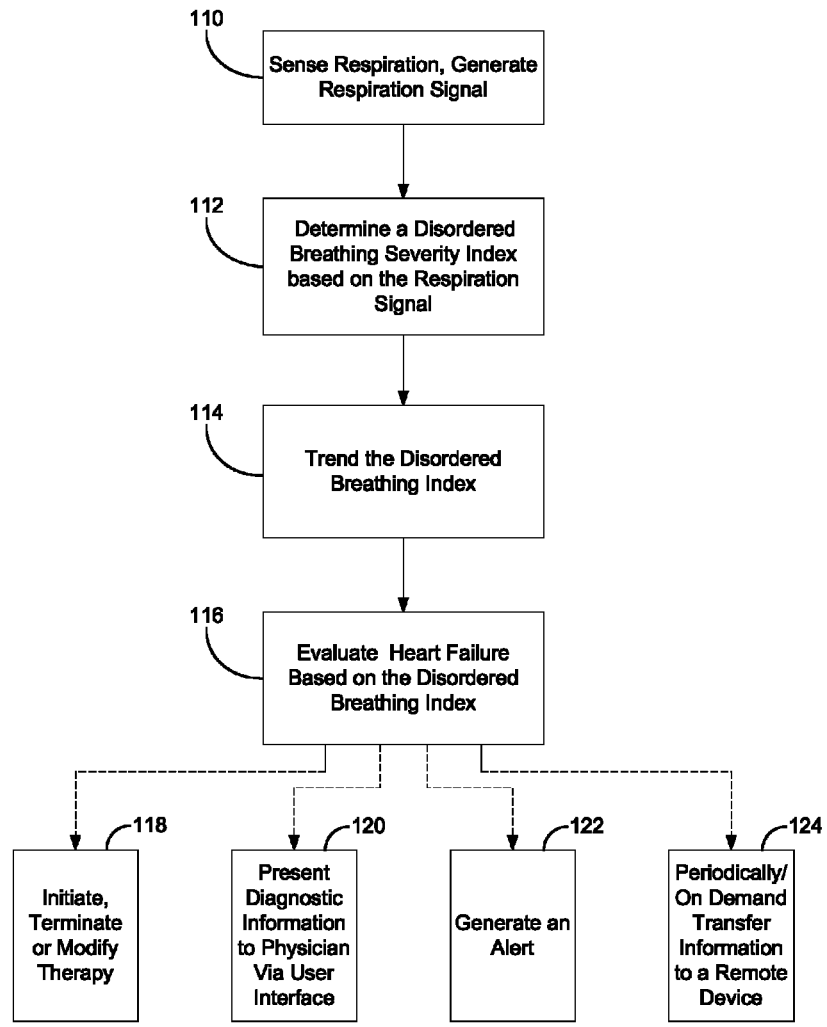
FIGS. 1A and 1B are methods for providing patient assessment in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Cardiac rhythm management (CRM) devices, such as pacemakers, defibrillators, and resynchronizers, may be used as a platform to deploy additional sensors for acquiring information useful in diagnosing and/or tracking a variety of patient symptoms or conditions in addition to cardiac conditions. For example, sensing circuitry disposed in conjunction with CRM circuitry may be used to detect disordered breathing (DB) conditions, such as apnea, rapid shallow breathing, and/or Cheyne-Stokes respiration. Detecting and evaluating DB may enable a clinician to more easily diagnose and track the progression of heart failure (HF) and/or symptoms associated with HF, such as edema, orthopnea, and/or dyspnea, including paroxysmal nocturnal dyspnea.

In accordance with embodiments of the invention, an implantable CRM device may monitor a patient's respiration, e.g., using transthoracic impedance sensors and/or other respiration sensors, to detect DB episodes and acquire other information related to the DB episodes. The DB information may be used to develop a DB index that quantifies some aspect of the patient's DB. The DB index may be trended over a period of time. The patient's HF status may be evaluated based on the DB trend and the evaluation may be presented to the clinician, possibly along with other information related to patient health.

The processes that provide HF evaluation in accordance with embodiments of the invention may be implemented using a single implantable device, or may be implemented using a system of multiple devices, such as multiple devices operating as an advanced patient management system. If multiple devices are used, the various processes described herein may be divided between the system components. An implanted device or a system of devices according to the present invention may include one or more of the features, structures, methods, or combinations thereof described herein. For example, a device or system may be implemented to include one or more of the described features and/or processes. It is intended that such a device or system need not include all of the features described herein, but may be implemented to include selected features that provide for unique structures and/or functionality. Such a device or system of devices may be implemented to provide a variety of diagnostic and/or therapeutic functions.

FIG. 1A illustrates a flowchart of a method for providing patient assessment in accordance with embodiments of the invention. The method includes sensing 110 patient respiration and generating a respiration signal. Disordered breathing episodes are detected based on the respiration signal. A DB index is developed 112 and is trended 114 over a period of time. The patient's HF status is evaluated 116 based on the DB trend.

Once the DB severity index is determined, the HF evaluation may involve one or more optional processes. For example, the device or system may initiate, terminate, or modify 118 a therapy delivered to the patient. In various configurations, the therapy may involve one or more of an electrostimulation therapy, such as cardiac electrostimulation, a nerve stimulation therapy, a drug therapy, a respiration therapy, a patient-external therapy, a patient-internal therapy, a combination of therapies, or other processes to treat patient conditions.

Information related to the DB trend and/or HF evaluation may be presented to a clinician, such as via a display or other user interface device. The DB trend/HF evaluation may be presented 120 along with other patient information such as medical history, disease etiology, previous and current therapies, data acquired or derived from other sensors, and/or other information related to, or unrelated to HF status. The DB trend/HF evaluation may involve, for example, one or more of metrics or evaluations derived from the DB trend, suggestions regarding diagnosis or treatment, comparisons with similarly situated patient populations, predictions regarding progression or outcomes, or other information of diagnostic or therapeutic value.

In some embodiments, an alert may be generated 122 based on the DB trend or HF evaluation. For example, the alert may be generated when the DB trend indicates a sudden change the patient's condition or a more gradual change beyond a threshold amount, or a change beyond a threshold for a predetermined length of time. The alert may be generated, for example, to indicate that the clinician or patient should take some action to alleviate the patient symptoms. The alert may comprise any perceivable stimulus, including an audible, visual, or vibratory alert. The alert may involve transmission of an alert message, such as via email, pager, and/or cellular telephone. In some embodiments, respiration information, DB index and/or HF evaluation information may be transferred 124 to a remote device either automatically according to a pre-established schedule, or on demand. For example, the respiration information, DB index and/or HF evaluation information may be transferred periodically or on command to a remote advanced patient management system.

In some embodiments, a subset of the functions of the heart failure assessment may be implemented in an implanted device and other functions implemented in a patient external device wirelessly coupled to the implanted device. In other embodiments, all of the heart failure assessment functionality is provided in an implanted device.

Figure 2A:
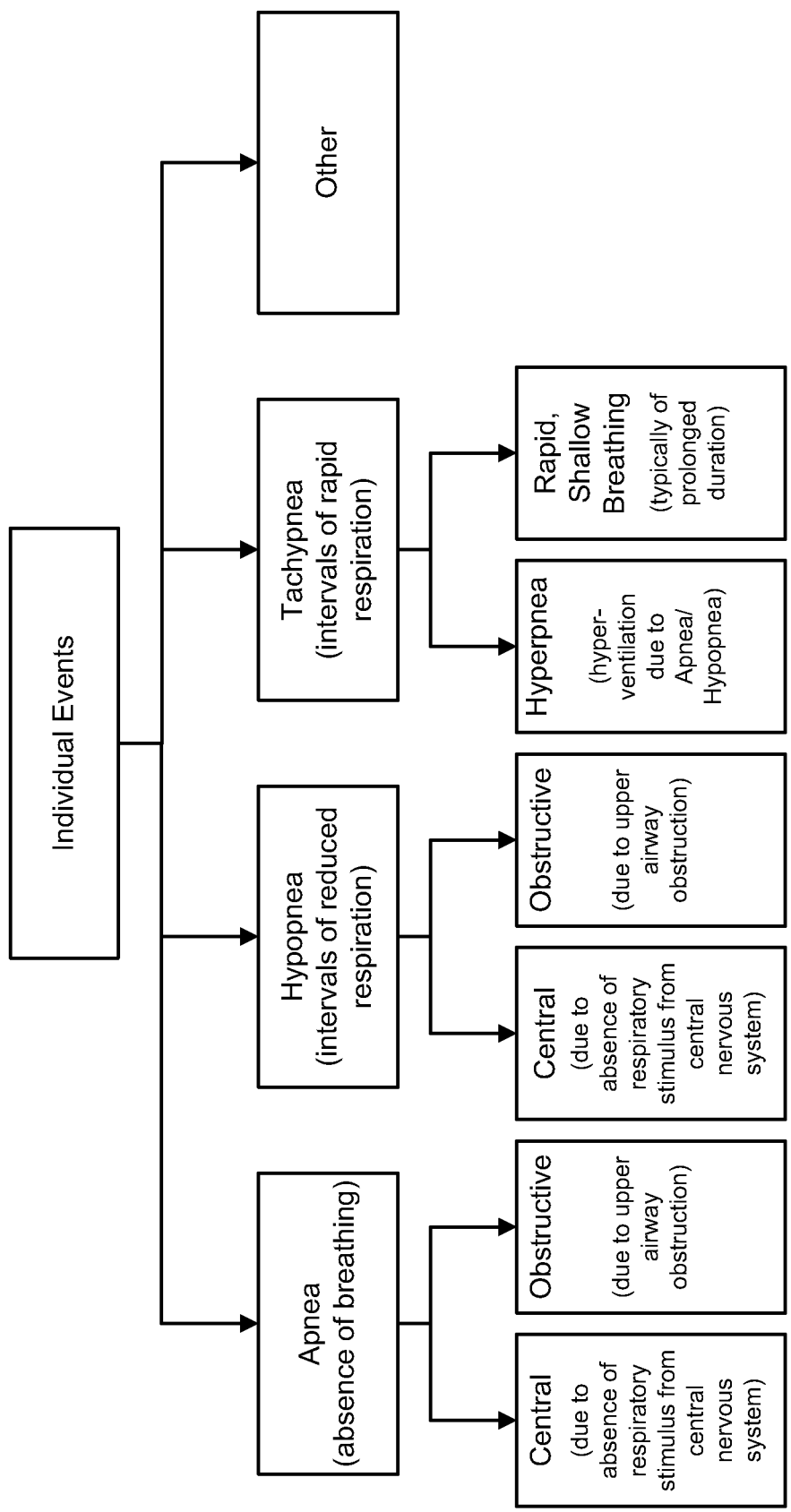
FIGS. 2A and 2B are charts illustrating classification of individual and periodically occurring disordered breathing events.
Figure 2B:
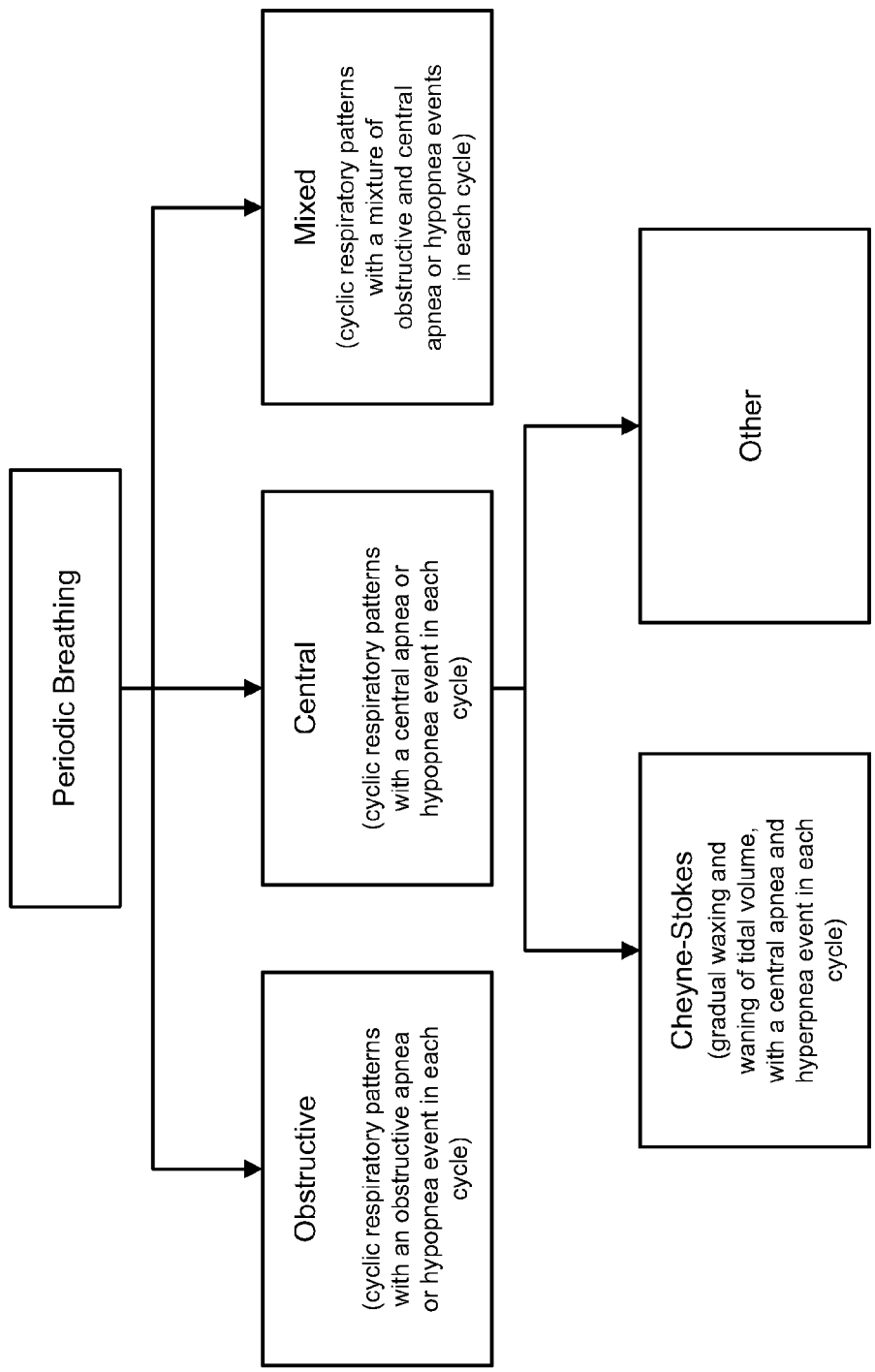

According to embodiments of the invention, the patient's transthoracic impedance may be sensed and used to generate a respiration signal. Various types and/or characteristics of disordered breathing may be determined based on the respiration signal. FIGS. 2A and 2B provide charts illustrating classification of individual disordered breathing events and series of periodically recurring disordered breathing events, respectively. As illustrated in FIG. 2A, individual disordered breathing events may be grouped into apnea, hypopnea, tachypnea and other disordered breathing events. Apnea events are characterized by an absence of breathing. Intervals of reduced tidal volume are classified as hypopnea events. Tachypnea events include reduced intervals of respiration associated with an elevated respiration rate.

As illustrated in FIG. 2A, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing, typically acutely after an apnea or hypopnea. A tachypnea event may alternatively be classified as rapid shallow breathing, typically of prolonged duration.

FIG. 2B illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central events in each cycle. Cheyne-Stokes is a particular type of periodic breathing involving a gradual waxing and waning of tidal volume and having a central apnea and hyperpnea event in each cycle. Other manifestations of periodic breathing are also possible. Disordered breathing episodes may be classified based on the characteristic respiration patterns associated with particular types of disordered breathing.

Using the respiration signal, a disordered breathing severity index may be generated. In one implementation, the disordered breathing severity index may be based on the number of disordered breathing occurrences over a period of time. In various implementations, the disordered breathing index used to assess HF may be an apnea index (AI, number of apnea events per unit time), a hypopnea index (HI, number of hypopnea events per unit time) or an apnea hypopnea index (AHI, the number of apnea and hypopnea episodes per hour). The disordered breathing index is representative of the severity of disordered breathing experienced by the patient, e.g., the severity of apnea or the severity of CSR. Other variables such as average duration of a disordered breathing event, number of apneic versus hypopneic events. Yet other variables relating to physiological parameters affected by disordered breathing may be used in the disordered breathing severity index. For example, the average decrease in blood oxygen saturation, a change in heart rate, a change in blood pressure, a change in electromyogram (EMG), and/or a change in electroencephalogram (EEG) during respiration events may also be used to determine the disordered breathing index.

Figure 1B:
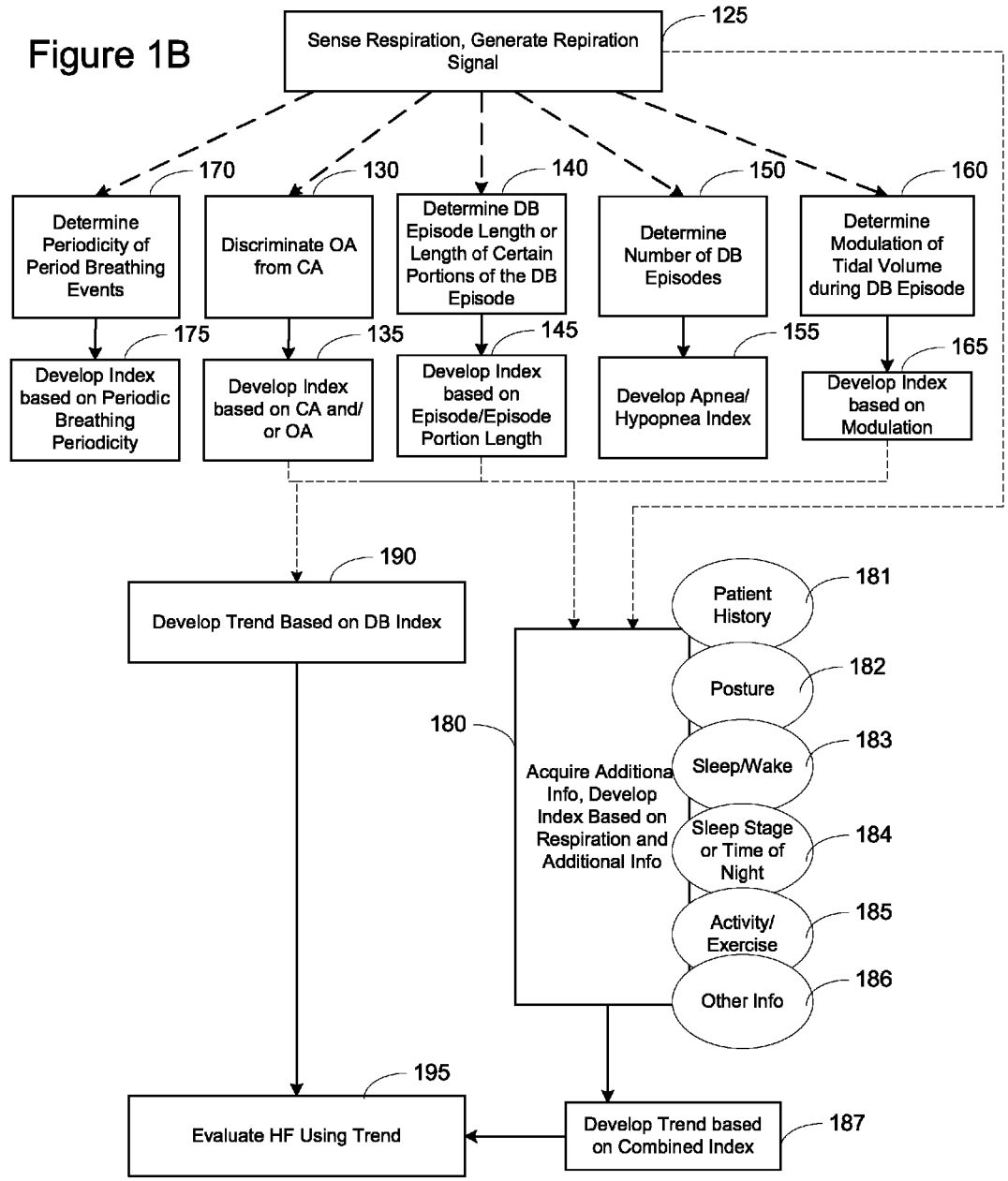

FIG. 1B illustrates a number of optional processes that may be employed to develop a DB index trend and to evaluate heart failure status in accordance with embodiments of the invention. The patient's respiration is sensed and a respiration signal is generated 125. Various optional processes 130-135, 140-145, 150-155, 160-165, 170-175 may be implemented to determine a disordered breathing index that quantifies some aspect of the patient's disordered breathing useful for evaluating HF status. The disordered breathing index may be trended 190 and used to evaluate 195 HF status.

According to one embodiment, the device or system may count 150 the number of DB episodes experienced by the patient. The DB index may be developed 155 as the number of DB episodes experienced by the patient within a specified period of time. In some implementations, the DB index may comprise an apnea/hypopnea index (AHI) which quantifies the number of apnea or hypopnea episodes experienced by the patient per hour.

According to one embodiment, development of the disordered breathing index may involve discriminating 130 between different types of disordered breathing based on origin. Obstructive and central disordered breathing can coexist in patients with HF. However, central disordered breathing is more closely associated with the progression of heart failure than obstructive disordered breathing. Thus, HF evaluation may be enhanced by using a DB index developed 135 based predominantly on information related to central disordered breathing episodes, without including obstructive disordered breathing information. Alternatively, HF evaluation may be performed using a DB index based on a ratio of central to obstructive DB, or other metrics that require discrimination between central and obstructive DB.

In some embodiments, the DB index may be developed based on characteristics of the respiration signal during the DB episode, such as timing and/or morphology characteristics of the respiration signal. For some patients, the length of DB episodes or of particular portions of the DB episodes may increase as HF worsens. In these situations, HF status may be determined based on an increase in the length of the DB episodes. As indicated as FIG. 1B, the HF evaluation process may involve determining 140 the length of the DB episodes experienced by the patient or determining the length of a portion or portions of the DB episodes. The length of the DB episodes or DB episodes portion(s) may be used to develop 145 the DB index.

In some embodiments, the DB index may relate to the modulation of respiration tidal volume during periodic breathing (PB) episodes such as Cheyne-Stokes respiration (CSR). An increase in tidal volume modulation during CSR has been shown to be correlated to a worsening of the patient's HF status. The modulation of the tidal volume of breath intervals during CSR (or other PB episodes) may be determined 160 based on the generated respiration signal. A DB index may be developed 165 that quantifies the degree or depth of tidal volume modulation during CSR.

Some patients may experience periodic breathing at fairly regular intervals. In some embodiments, a DB index may be developed 190-195 based on the periodicity of the periodic breathing pattern.

In some embodiments, the generated respiration signal and/or one or more DB indices may be combined 187 with additional information related to disordered breathing and/or to the patient's health status to evaluation HF status. Various additional information may be acquired 180 via sensors, questionnaires, and/or other information gathering processes. A representative list of information that may be combined with the DB index includes, but is not limited to, patient medical history information 181, posture during DB episodes 182, whether the patient is asleep or awake during DB episodes 183, time of night/day that DB occurs 184, sleep stage during DB episodes 184, whether or not the patient is active or inactive during DB episodes 185, and/or other information 186, such as cardiac flow, cardiac pressure, edema, blood electrolyte levels, blood neurohormone information, that serves to provide the context of the patient's situation during disordered breathing episodes.

Information about the context surrounding the DB episodes affecting the patient may be used to enhance the evaluation of HF status. An index or other metric may be determined 180 based on patient respiration and the additional information. The combined index may be used to develop 187 a trend and HF status of the patient may be evaluated 195 based on the trend.

Disordered breathing that occurs while the patient is active, such as during a period of time the patient is exercising, is less symptomatic of HF progression than DB episodes that occur during sleep or periods of rest. Thus, the HF evaluation processes may involve acquiring 185 additional information from an activity sensor used to indicate the level of patient activity during a detected DB episode. DB episodes that occur when the patient is very active may be ignored, or may be given less weight than DB episodes that occur when the patient is asleep or at rest.

In another example, assessment of the patient's overall health may involve tracking changes in the level of patient activity over a period of time. A sudden or progressive decline in overall patient activity may be an indication of HF decompensation. Correlating changes in DB to patient activity may provide an early warning with respect to sudden HF decompensation, possibly allowing time for clinician response and/or therapy modification to mitigate the effects of decompensation. For example, a metric or index based on a combination of patient activity and DB characteristics may be developed that allows earlier identification of patients in danger of a sudden worsening of HF symptoms. The combined metric or index may be compared to a threshold used for triggering an alert if a rapid increase in the severity of symptoms related to HF is detected.

In one embodiment, the additional information may be acquired 181 from the patient via a medical history questionnaire or other patient input. The additional information may relate to the patient's medical history, patient etiology and/or comorbidities (e.g., atrial fibrillation (AF), chronic obstructive pulmonary disease (COPD), renal disease, etc.), mode of progression to decompensation, perception of labored breathing (dyspnea), and/or current HF status. The additional information may be factored into a metric or other index and used in HF evaluation, or may be used to modify a threshold used in connection with generating an alert or providing therapy, for example.

In one embodiment, the DB episode information may be used in combination with acquired information that relates to the sleep/wake status 183 and/or time of night or sleep stage 184 of the patient. As previously described, DB episodes that occur during sleep may be more symptomatic of HF progression than DB episodes that occur when the patient is awake and active. In addition, DB episodes that occur during certain sleep stages or certain times of the night may be more symptomatic of worsening HF status than DB episodes that occur during other sleep stages. For example, DB episodes that occur during rapid eye movement (REM) sleep may be less associated with HF than DB episodes that occur during more quiescent sleep stages, such as state 3 or stage 4 sleep.

In one embodiment, the HF evaluation process may detect DB episodes, detect sleep stage, and correlate the DB episodes to sleep stage. An index or other metric may be developed based on the correlation of DB episodes to sleep stage. For example, a DB index may be developed using weighted coefficients applied to a number or severity index of DB episodes occurring during various states of sleep or wakefulness. For example, the coefficient applied to the number or severity index of DB episodes occurring during non-REM sleep may be higher than the coefficient applied to the number or severity index of DB episodes occurring during REM sleep and the number or severity index of DB episodes occurring during awake rest may be greater than the coefficient applied to the number or severity index of DB episodes occurring while the patient is active. Expressed mathematically, the combined DB index may be developed as in Equation 1:

$$DB_{index} = a_1 DB_{Non\text{-}REM} + a_2 DB_{REM} + f(a) DB_{awake} \qquad [1]$$

where $a_1$ and $a_2$ are constant coefficients, $DB_{Non\text{-}REM}$ is the disordered breathing index associated with disordered breathing episodes occurring in non-REM sleep, $DB_{REM}$ is the disordered breathing index associated with disordered breathing episodes occurring during REM sleep, $DB_{awake}$ is the disordered breathing index associated with disordered breathing episodes occurring while the patient is awake, and $f(a)$ is a function of the patient activity.

As previously discussed, obstructive and central disordered breathing may coexist in some HF patients. It has been observed that the disordered breathing experienced by the patient may shift during the night from predominantly obstructive DB during the first portion of the night to predominately central disordered breathing during the second portion of the night. The shift in DB type may be caused by a reduction in $PCO_2$, related to deterioration of cardiac function during the night. In some embodiments, an index or metric may be developed that correlates DB episode information with the time of night that the DB occurs. In this embodiment, DB occurring during the later portion of the night, which is more likely to be central DB, may be factored in more heavily than DB occurring during the earlier portion of the night, which is more likely to be obstructive DB. In other embodiments, a DB trend may be developed based on the time of night that the DB transitions from predominantly obstructive DB to predominately central DB.

In one embodiment, posture information may be acquired 182 and correlated with DB. HF patients typically experience orthopnea, which is difficulty in breathing unless standing or sitting up. Disordered breathing may increase in HF patients when they are reclining or lying down due to an increase in pulmonary congestion that occurs during these postures. As a result, many HF patients sleep sitting up, or sleep with their torso propped up on several pillows. A DB index, e.g., based on the frequency, pattern, and/or length of DB episodes, may be enhanced by factoring in the posture or tilt angle of the patient during the DB episodes. For example, a DB index may be developed using respiration information that takes also takes into account tilt angle, providing a more accurate assessment of changes in frequency and/or length of DB episodes.

In one example, a DB index may be developed as a modified apnea/hypopnea index, where each DB episode is weighted by a factor associated with the tilt angle of the patient during the DB episode. In one scenario, DB episodes occurring when the patient is standing or sitting upright (tilt angle=90°) are multiplied by a weighting factor of 1, DB episodes occurring when the patient is lying down (tilt angle=0°) are multiplied by a factor of 0, with the weighting factors of tilt angles between 90° and 0° scaled accordingly. Using this scheme, DB episodes that occur while the patient is standing or sitting upright are counted as more significant than episodes occurring when the patient is lying down.

In another example, multiple DB indices may be developed for particular tilt angles. For example, one DB index, such as the AHI, may be calculated based on DB episodes occurring while the patient posture corresponds to a first tilt angle or tilt angle range. A second AHI may be calculated based on DB episodes occurring while the patient posture corresponds to a second tilt angle or tilt angle range, and so forth. Several of the posture corrected AHIs may be added, averaged, or otherwise combined, and the result may be trended and used for HF evaluation.

Figure 3:
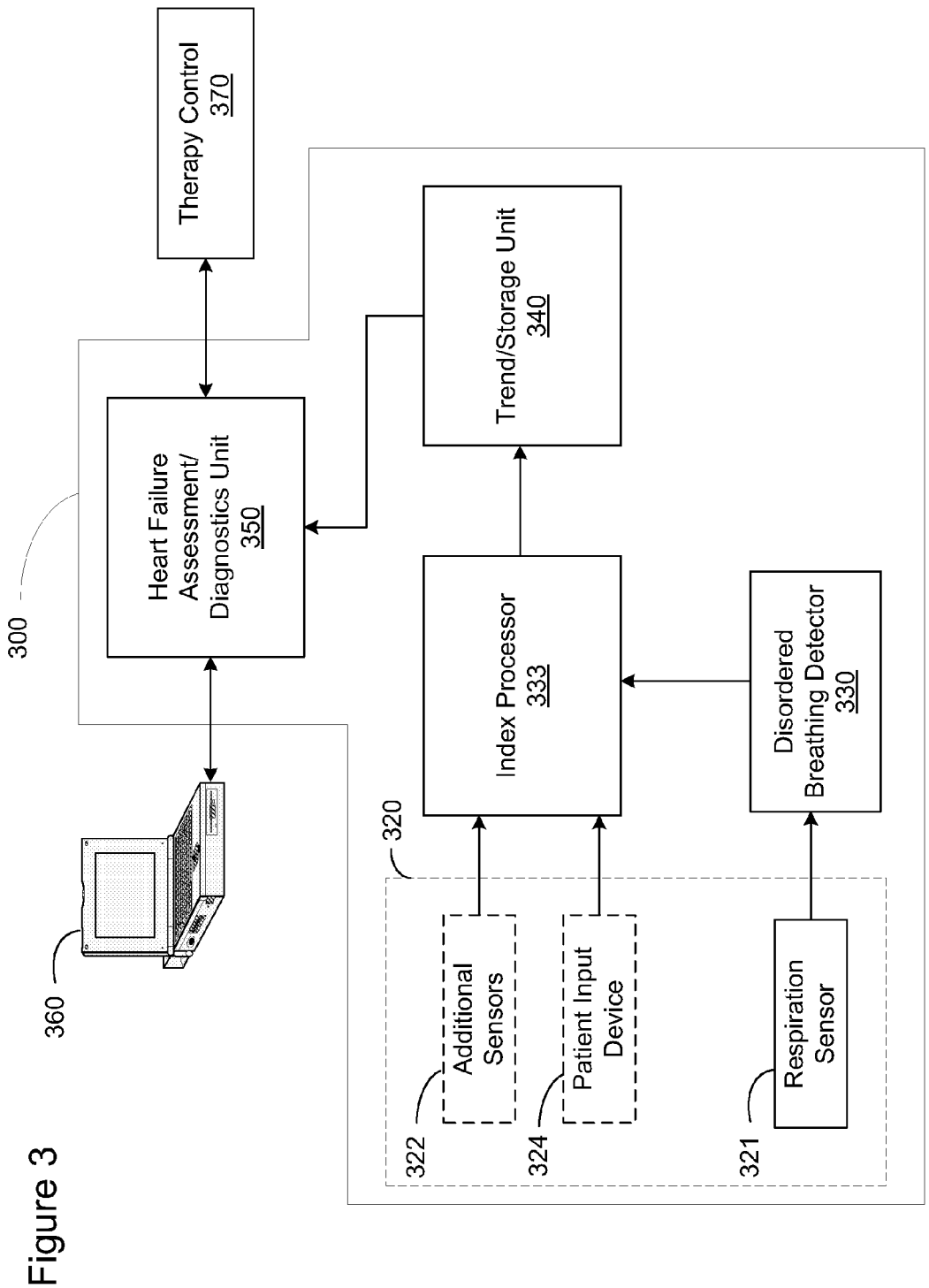
FIG. 3 is a block diagram of a medical system that may be used to implement a system for heart failure status evaluation in accordance with embodiments of the invention.

FIG. 3 is a block diagram of an HF evaluation system 300 that may be used to implement the methodologies of the present invention. The system includes a data acquisition module 320 that comprises at least a respiration sensor 321 configured to sense patient respiration and generate a respiration signal. In accordance with some embodiments, an implantable transthoracic impedance sensor such as the type of sensor used in rate adaptive pacemakers may be used to generate a respiration signal. Disordered breathing episodes may be detected by a disordered breathing detector 330. The disordered breathing detector 330 may be configured to recognize the respiration patterns, e.g., breath rate and/or tidal volume patterns, characteristic of various forms of disordered breathing, including apnea, hypopnea, CSR, periodic breathing, hyperpnea, and/or other DB patterns.

In some embodiments, the information from the disordered breathing detector 330 is used by the index processor 333 to determine a DB index that characterizes the disordered breathing experienced by the patient. For example, in one embodiment, index processor 333 calculates a DB index, such as an AHI, that reflects the number of DB episodes experienced by the patient over a period of time. In another embodiment, the index processor 333 determines a DB index that is based on lengths of the DB episodes or lengths of certain portions the DB episodes.

In one embodiment, the index processor 333 may discriminate DB episodes that are centrally mediated from DB episodes caused by breathing obstructions. The index processor 333 may determine an index based on one or both of these DB types.

In one embodiment, the index processor 333 may process the respiration signal to determine the tidal volume of one or more breath intervals during a DB episode. The index processor 333 may determine the degree of modulation of the patient's tidal volume during DB and may develop an index based on the degree of modulation.

In one implementation, the data acquisition module 320 may incorporate additional sensors 322 configured to acquire information related to patient posture, activity, sleep state, time of night, sleep stage and/or other sensed information. The data acquisition module 320 may also include an input device 324 capable of receiving patient information, such as medical history information recorded from a questionnaire. The additional information may be used in conjunction with the respiration information, for example, to form a combination index based on the DB episode information and the additional information.

A storage/trend unit 340 may store indices and/or may develop and store a trend or trends based on the indices determined by the index processor 333. The trend information may be used by an HF diagnostics unit 350 to evaluate HF status and/or to track the progression of HF decompensation and/or to perform other diagnostic functions. The trends developed as described herein may be used in a number of ways to assist in the diagnosis and/or treatment of patients suffering from HF and/or other respiratory or cardiopulmonary disorders. According to one aspect of the invention, the trend information may be presented to a patient's physician for use in making diagnosis and/or therapy decisions. In one implementation, trend information developed by the trend/storage unit 340 may be configured by the diagnostics unit 350 for presentation for viewing on demand by the physician via a display of a device programmer 360 or other remote device. The physician may use the trend information to diagnose the patient and/or to initiate, terminate or modify therapy delivered to the patient. In some implementations, the HF evaluation system 300 may communicate with a remote device, such as the device programmer 360 or advanced patient management system (APM) to download trend information periodically so that current trend information is available to the physician.

According to another aspect, the trend information may be used by the diagnostics unit 350 to automatically make a diagnosis and/or to automatically develop a control signal that is coupled to therapy control circuitry 370. The control signal may and direct the therapy control circuitry 370 to initiate, terminate, or modify therapy, such as a cardiac electrostimulation therapy, a drug therapy, a respiration therapy, and/or other types of therapy.

The diagnostics unit 350 may compare the trends developed as described in the various embodiments, to one or more thresholds. The diagnostics unit 350 may detect or diagnose the presence of HF, may determine the progression or regression of HF symptoms, and/or may determine if therapy should be modified based on the comparison.

If the HF evaluation system 300 automatically produces a diagnosis, the diagnosis may be displayed or otherwise provided on demand, or in the form of an automatic alert generated when patient conditions indicate that the patient symptoms have deteriorated beyond a trigger level. If the diagnostics unit 350 automatically initiates, terminates, or modifies therapy, the diagnostics unit 350 may develop a control signal transmitted to one or more therapy control units 370 indicating the therapy change. The control signal may be generated by the diagnostics unit 350 based on trend information developed from one or more indices.

For example, if the HF evaluation system 300 produces a control signal coupled to the therapy control circuitry of a CRM device, the control signal may control modification of various pacing parameters. In such an implementation, the therapy modification may include changing the pacing mode, e.g., switching pacing from single ventricular pacing to biventricular pacing, changing the pacing site, changing pacing rate, and/or modifying various pacing delays such as the atrioventricular pacing delay and/or the interventricular pacing delay.

In another example, if the HF evaluation system 300 is used in conjunction with an implantable drug delivery device, such as a drug pump, the HF evaluation system 300 may automatically modify the type and/or titration of drugs used to treat HF or symptoms of HF. Alternatively, the HF evaluation system 300 may inform the patient that their medication should be changed. The automatic therapy modification may be remotely reviewed and approved by the patient's physician prior to making or suggesting the modification.

Figure 4:
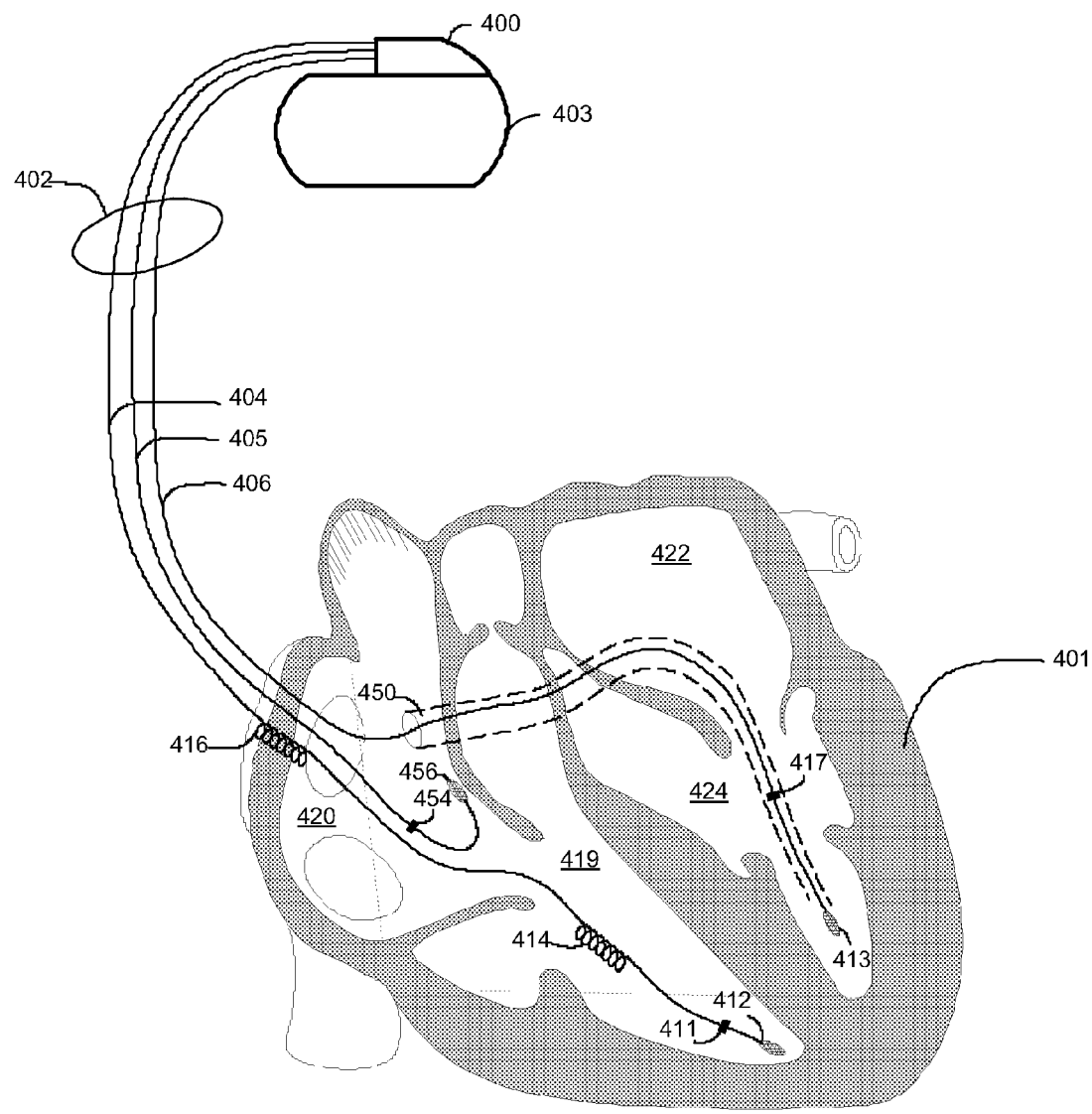
FIG. 4 is a partial view of one embodiment of an implantable medical device in accordance with embodiments of the invention.

Referring now to FIG. 4 of the drawings, there is shown a CRM device that may be used to implement HF evaluation processes in accordance with the present invention. The CRM device illustrated in FIG. 4 includes an implantable cardioverter/defibrillator (ICD) 400 electrically and physically coupled to a lead system 402.

Portions of the intracardiac lead system 402 are inserted into the patient's heart 490. The intracardiac lead system 402 includes one or more electrodes configured to sense electrical cardiac activity of the heart 401, deliver electrical stimulation to the heart 401, sense the patient's transthoracic impedance, and/or sense other physiological parameters, e.g., thoracic, cardiac or vascular pressure, temperature or other physiological parameters. Portions of the housing 403 of the ICD 400 may optionally serve as a can electrode.

In the embodiment shown in FIG. 4, the lead system 402 includes an intracardiac right ventricular (RV) lead system 404, an intracardiac right atrial (RA) lead system 405, and an intracardiac left ventricular (LV) lead system 406.

The right ventricular lead system 404 illustrated in FIG. 4 includes an SVC-coil 416, an RV-coil 414, an RV-ring electrode 411, and an RV-tip electrode 412. The right ventricular lead system 404 extends through the right atrium 420 and into the right ventricle 419. In particular, the RV-tip electrode 412, RV-ring electrode 411, and RV-coil electrode 414 are positioned at appropriate locations within the right ventricle 419 for sensing and delivering electrical stimulation pulses to the heart. The SVC-coil 416 is positioned at an appropriate location within the right atrium chamber 420 of the heart 401 or a major vein leading to the right atrial chamber 420 of the heart 401.

In one configuration, the RV-tip electrode 412 referenced to the can electrode may be used to implement unipolar pacing and/or sensing in the right ventricle 419. Bipolar pacing and/or sensing in the right ventricle may be implemented using the RV-tip 412 and RV-ring 411 electrodes. In yet another configuration, the RV-ring 411 electrode may optionally be omitted, and bipolar pacing and/or sensing may be accomplished using the RV-tip electrode 412 and the RV-coil 414, for example. The right ventricular lead system 404 may be configured as an integrated bipolar pace/shock lead. The RV-coil 414 and the SVC-coil 416 are defibrillation electrodes.

The left ventricular lead 406 includes an LV distal electrode 413 and an LV proximal electrode 417 located at appropriate locations providing electrical coupling to the left ventricle 424 for pacing and/or sensing the left ventricle 424. The left ventricular lead 406 may be guided into the right atrium 420 of the heart via the superior vena cava. From the right atrium 420, the left ventricular lead 406 may be deployed into the coronary sinus ostium, the opening of the coronary sinus 450. The lead 406 may be guided through the coronary sinus 450 to a coronary vein of the left ventricle 424. This vein is used as an access pathway for leads to reach the surfaces of the left ventricle 424 which are not directly accessible from the right side of the heart. Lead placement for the left ventricular lead 406 may be achieved via subclavian vein access and a preformed guiding catheter for insertion of the LV electrodes 413, 417 adjacent to the left ventricle.

Unipolar pacing and/or sensing in the left ventricle may be implemented, for example, using the LV distal electrode referenced to the can electrode. The LV distal electrode 413 and the LV proximal electrode 417 may be used together as bipolar sense and/or pace electrodes for the left ventricle. The left ventricular lead 406 and the right ventricular lead 404, in conjunction with the ICD 400, may be used to provide cardiac resynchronization therapy such that the ventricles of the heart are paced substantially simultaneously, or in phased sequence separated by in interventricular delay, to provide enhanced cardiac pumping efficiency for patients suffering from HF.

The right atrial lead 405 includes a RA-tip electrode 456 and an RA-ring electrode 454 positioned at appropriate locations in the right atrium 420 for sensing and pacing the right atrium 420. In one configuration, the RA-tip 456 referenced to the can electrode, for example, may be used to provide unipolar pacing and/or sensing in the right atrium 420. In another configuration, the RA-tip electrode 456 and the RA-ring electrode 454 may be used to effect bipolar pacing and/or sensing.

The ICD 400 may include sensing circuitry for sensing patient respiration. The respiration sensor may be configured, for example, using the intracardiac electrodes to develop the transthoracic impedance signal which tracks respiration. Respiration sensor drive circuitry disposed within the CRM housing 403 provides the necessary drive signals to activate drive electrodes. Response signals are sensed via sense electrodes and are conditioned by the respiration sense circuitry.

The ICD 400 and lead system 402 may be used to support various sensors in addition to the cardiac and respiration sensors previously described. For example, patient activity may be detected using an accelerometer disposed within the ICD housing 403. Patient posture may be determined using a multiaxial sensor responsive to the orientation of the patient's body with respect to a gravitational field. Sleep state may be detected, for example, using a combination of respiration and patient activity, as described in commonly owned U.S. Publication No. 2005/0043652, which is incorporated herein by reference. REM sleep may be detected using a strain gauge or electromyogram (EMG) sensor positioned on the ICD housing 400 or lead system 402 as described in commonly owned U.S Patent Publication No. 2005/0043652, which is incorporated herein by reference. Sleep stage may alternatively be sensed via electroencephalogram (EEG), for example.

Figure 5A:
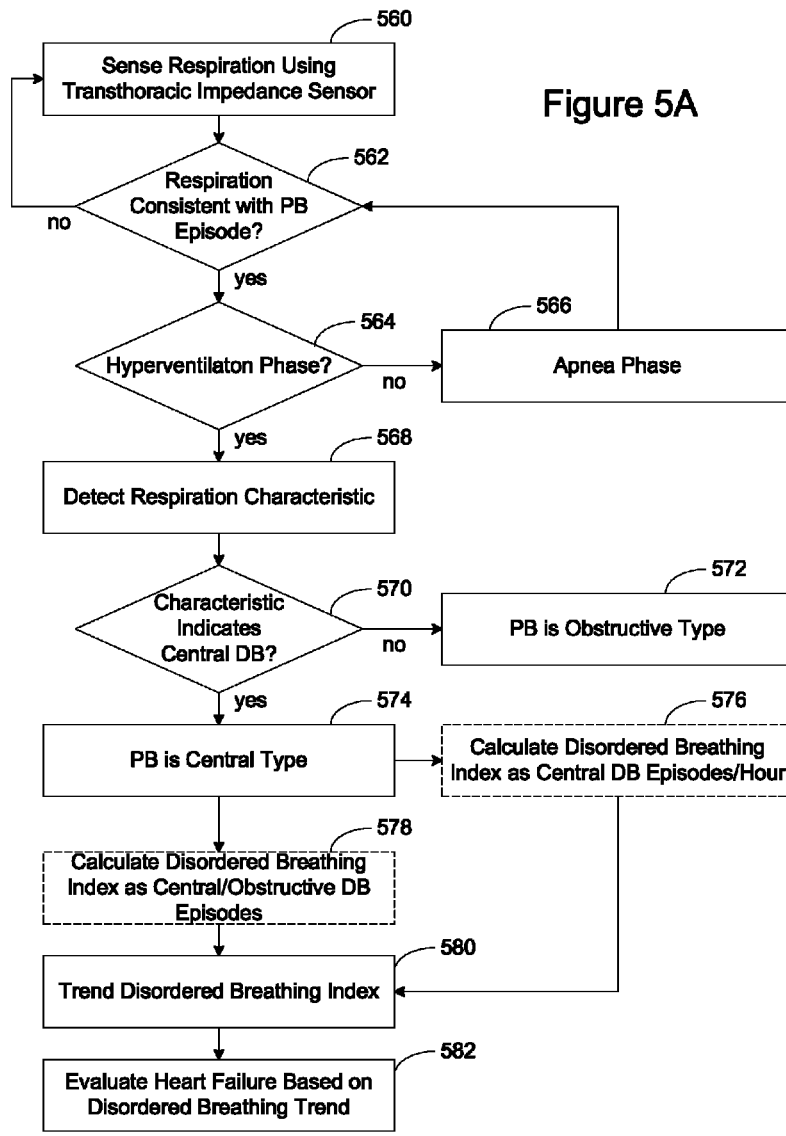
FIGS. 5A and 5B are flowcharts of methods for evaluating heart failure status using a disordered breathing index determined based on discrimination of obstructive disordered breathing event and central disordered breathing events in accordance with embodiments of the invention.
Figure 5B:
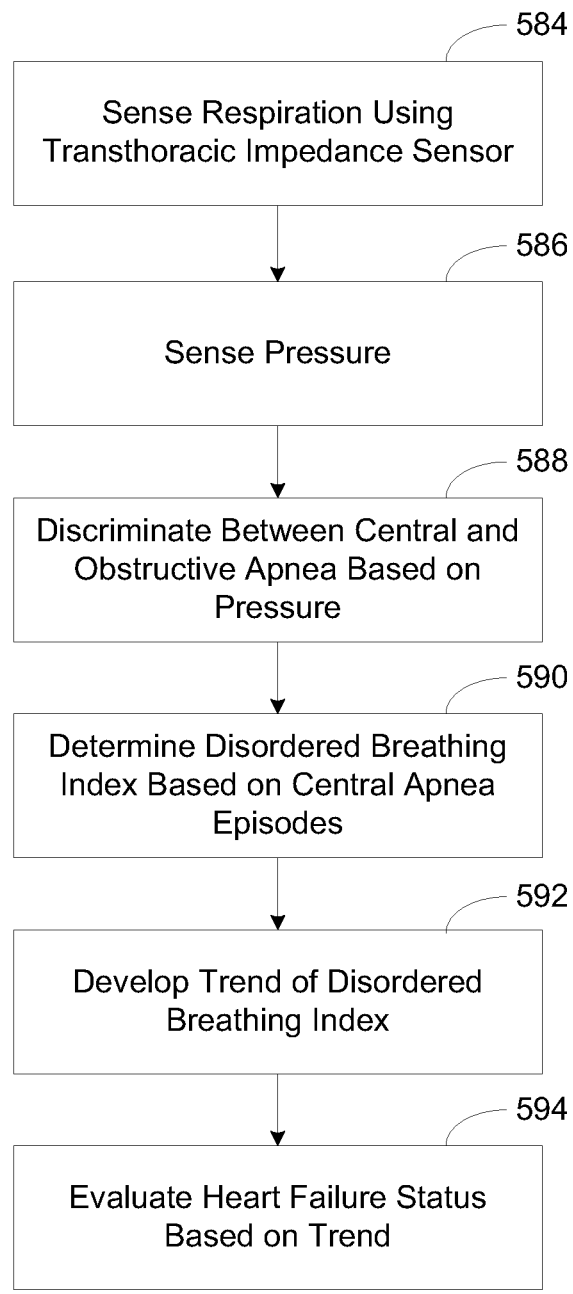

FIGS. 5A and 5B are flowcharts illustrating various implementations for evaluating HF status using a DB index determined based on discrimination between central and obstructive DB types. As previously mentioned, periodic breathing, such as CSR, is associated with a respiration pattern that includes periods of waxing tidal volume (hyperventilation portions) and periods of waning tidal volume (apneic portions). In some embodiments, obstructive DB is discriminated from central DB based on one or more characteristics of the hyperventilation phase of the periodic breathing. For example, central DB may be discriminated from obstructive DB based on the suddenness of the transition from apnea to hyperventilation. For obstructive DB, these transitions are more pronounced and sudden in comparison to the transitions in central DB episodes, which are more gradual. In one implementation, discrimination between obstructive and central DB may be performed based on the location of the centroid of the modulated waveform of CSR with respect to tidal volume during the hyperventilation portions of the CSR episode. The centroid of the respiration signal with respect to tidal volume during hyperventilation portions of obstructive DB is expected to have a smaller time coordinate and a larger amplitude coordinate when compared to the respiration signal of central DB.

In accordance with another implementation, illustrated in FIG. 5A, discrimination between central and obstructive disordered breathing is based on the characteristics of the hyperventilation phase of periodic breathing (PB). In this implementation, patient respiration is sensed 560 using a transthoracic impedance sensor and a respiration signal is generated. Periodic breathing is detected 562 based on a characteristic PB breathing pattern involving alternating patterns of hyperpnea 564 or apnea 566. During the hyperventilation phase 564, of the PB episode, at least one characteristic of the hyperventilation phase is detected and is used to discriminate 570 central DB from obstructive DB.

Various characteristics of the hyperventilation phase may be used to discriminate central DB from obstructive DB, including respiration rate during the hyperventilation phase, rate of increase in respiration rate during the hyperventilation phase, number of breaths in the hyperventilation phase, duration of the hyperventilation phase, among other characteristics. For example central DB may be discriminated from obstructive DB if the respiration rate during the hyperventilation phase is more than about 6 breaths per minute, versus obstructive DB with a rate of about 4 breaths per minute. If the respiration rate is above the threshold, the DB is determined to be 572 obstructive DB. If the respiration rate is equal to or below the threshold, the DB is determined to be 574 central DB.

According to one optional process, indicated by the dashed box 576, a DB index may be calculated based the number of central DB episodes detected. According to another optional process, indicated by the dashed box 578, the DB index may be calculated as the ratio of the number of central DB episodes to the number of obstructive DB episodes.

A trend may be developed 580 based on the DB index calculated 576, 578 by either of the optional processes. The patient's HF status may be evaluated 582 based on the DB episode trend.

FIG. 5B illustrates another method of evaluating HF status based on discrimination of central and obstructive DB. As described before, patient respiration is sensed 584 via a transthoracic impedance sensor which generates a respiration signal. The intrathoracic or intracardiac pressure may be sensed 586, e.g., via a pressure sensor, such as a thoracic, cardiac or vascular pressure sensor, disposed within the heart, within the cardiac vasculature, or the chest cavity. The pressure sensor may be mounted in or on a lead of the CRM device, or separate from the CRM device.

Obstructive DB causes a change in intrathoracic or intracardiac pressure which is detectable by the pressure sensor. Detection of a DB episode with a corresponding increase in pressure may be used to discriminate 588 obstructive DB episodes from central DB episodes. A DB index may be determined 590 based on the number, length, frequency, pattern, and/or severity of central DB episodes, or on a ratio of central to obstructive episodes, for example. A trend may be developed 592 based on the DB index. The patient's HF status is evaluated 594 based on the DB index trend.

In some embodiments, a DB index may be determined based on the lengths of DB episodes, such as the length of apnea episodes, the length of CSR episodes. For DB episodes including multiple disordered breathing patterns, such as CSR, the DB index may be calculated based on the length of certain portions of CSR episodes.

Figure 6A:
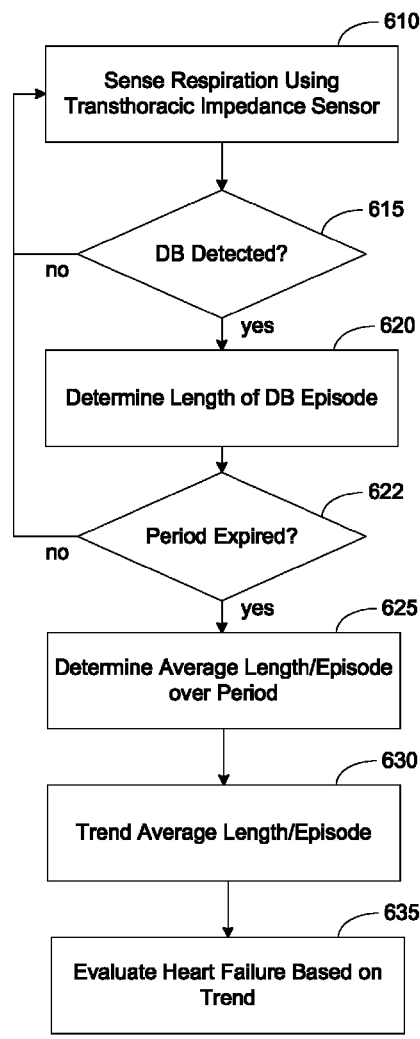
FIGS. 6A and 6B are flowcharts of methods for evaluating heart failure status using disordered breathing indices determined based on lengths of disordered breathing episodes or lengths of certain portions of disordered breathing episodes, respectively, in accordance with embodiments of the invention.
Figure 6B:
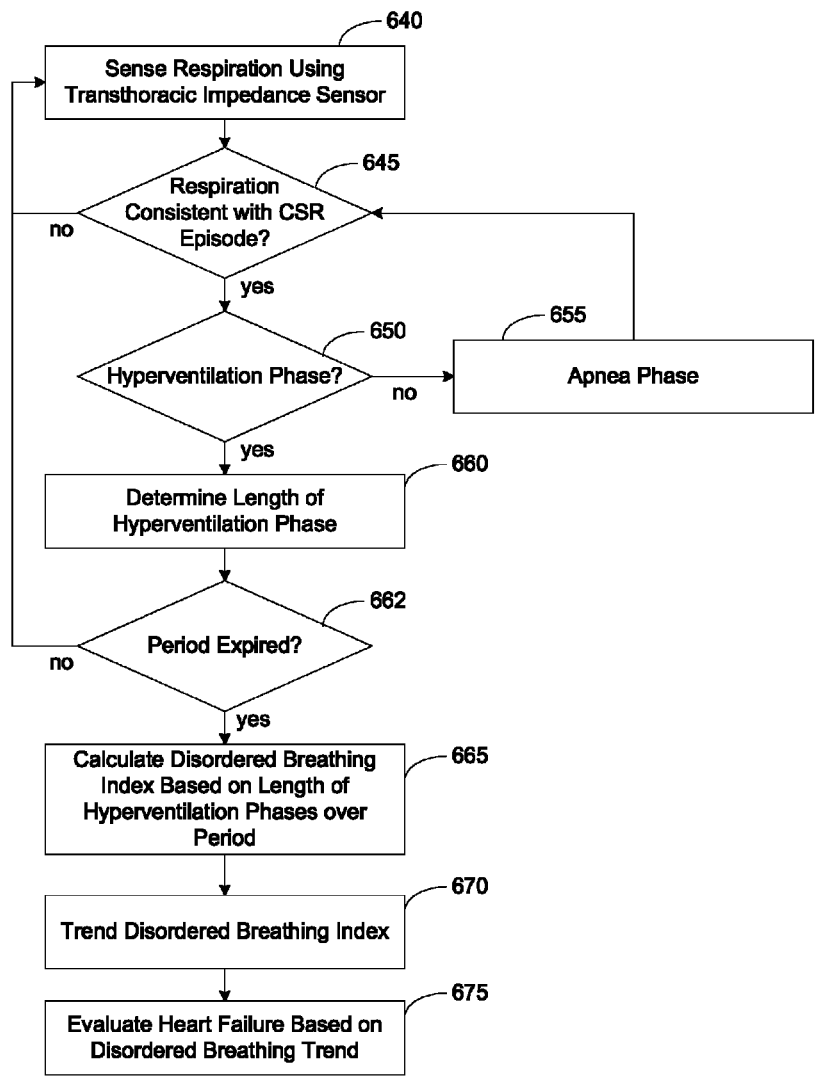
Figure 6C:
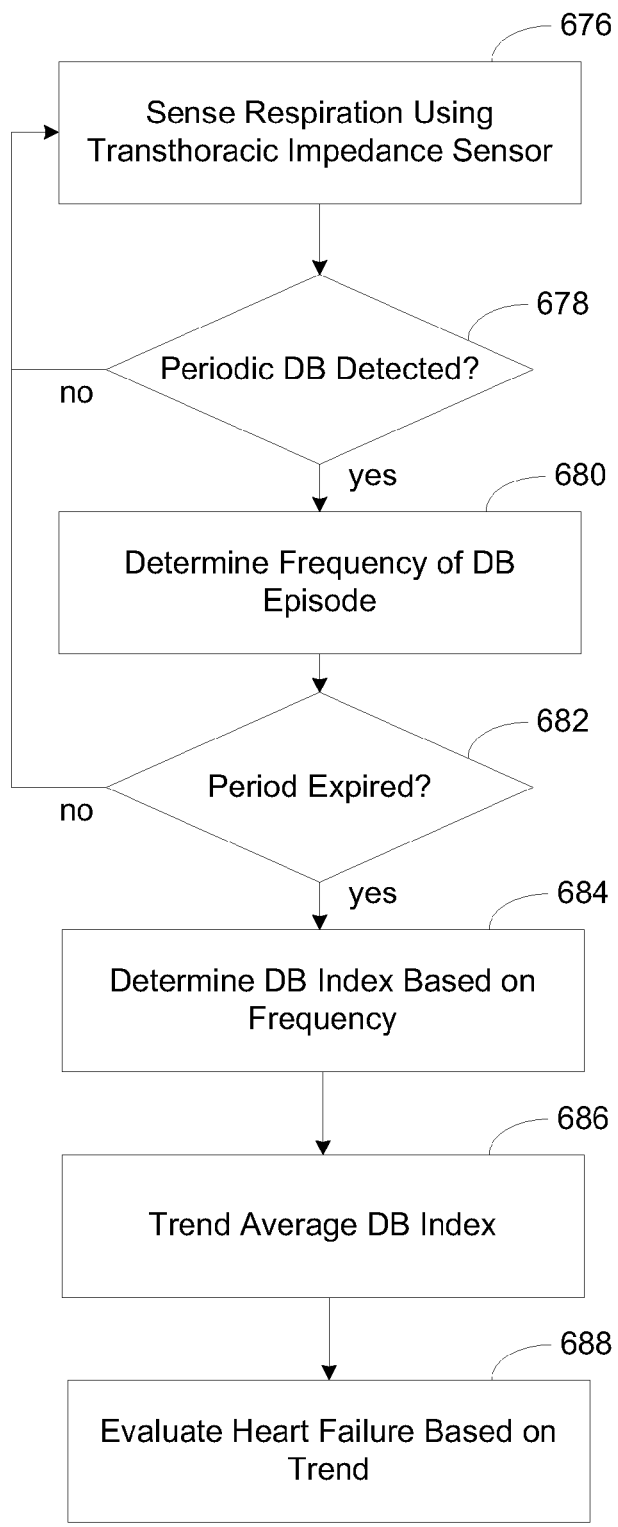
FIG. 6C is a flowchart of a method for evaluating heart failure status based on frequency of disordered breathing in accordance with embodiments of the invention.

Exemplary implementations of these methods are illustrated in FIGS. 6A, 6B and 6C. In the method illustrated by 6A, a DB index is calculated based on the average length of DB episodes of any origin experienced by the patient. A respiration signal is generated 610 and DB episodes are detected 615. For example, various DB episodes may be detected based on the characteristic respiration patterns associated with the various types of DB. The lengths of the DB episodes during a particular period are determined 620. The DB index is calculated for the period 622, which may be daily, weekly, monthly, or according to some other time period. As illustrated in FIG. 6A, an average length over the period may be calculated 625 as the DB index, although other statistical values, such as a mean length, maximum length or other value based on length may be used calculated as the DB index for the period. A trend is developed 630 based on the metric. The patient's HF status is evaluated 635 based on the trend.

FIG. 6B illustrates a method of calculating a DB index based on the length of portions of a DB episode. In this example, the DB index is based on the hyperventilation portions of CSR. Respiration is sensed 640 via a transthoracic impedance sensor and the characteristic CSR pattern is detected 645. The hyperventilation portions 650 of CSR are discriminated from the apneic portions 655 of CSR based on the rapid respiration rate associated with hyperventilation. The lengths of the hyperventilation portions are determined 660. The average length, mean length, maximum length, or some other length-based metric of the hyperventilation portions is calculated 665 over the period of interest 662, which may be hourly, nightly, daily, weekly, or according to some other time period. A trend is developed 670 based on the metric. The patient's HF status is evaluated 675 based on the trend.

Figure 6D:
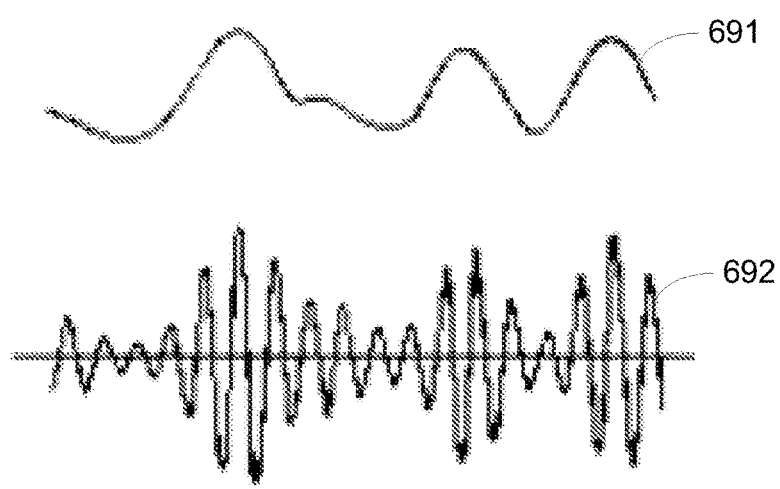
FIG. 6D is a graph illustrating frequency components of a Cheyne Stokes respiration signal which may be used to track HF progression in accordance with embodiments of the invention.

In some embodiments, the DB index may be calculated based on the pattern of DB episodes. For example, PB episodes, such as CSR, include a series of apneic and hyperventilation portions. The resultant respiratory pattern is illustrated in FIG. 6D. The pattern involves a lower frequency signal 691, which is the CSR pattern of waxing and waning tidal volume, modulating a higher frequency signal 692 derived from the breath cycles. During CSR, the respiration signal, which may have a frequency range of about 0.1 to about 1 Hz may be modulated by CSR having a frequency range of about 0.05 to about 0.01 Hz. Changes in the modulating frequency 691 may be used to track HF. Lower frequency signals are associated with central DB, which in turn is more closely related to HF than other types of DB. Progression of HF may be detected based on changes in the low frequency envelope of CSR.

FIG. 6C illustrates a method of calculating a DB index based on the modulating frequency of DB episodes, such as CSR episodes. Respiration is sensed 676 via a transthoracic impedance sensor. The periodic portion of DB episode is discriminated 678 from non-periodic portions. The modulating frequency of the periodic portion of DB episodes is measured 680 during the periodic portions. The average frequency, mean frequency, maximum frequency or some other frequency-based metric is calculated 684 for the modulating frequency of the DB episodes over the period of interest 682, which may be hourly, nightly, daily, weekly, or according to some other time period. A trend is developed 686 based on the DB index. The patient's HF status is evaluated 688 based on the trend.

Figure 7A:
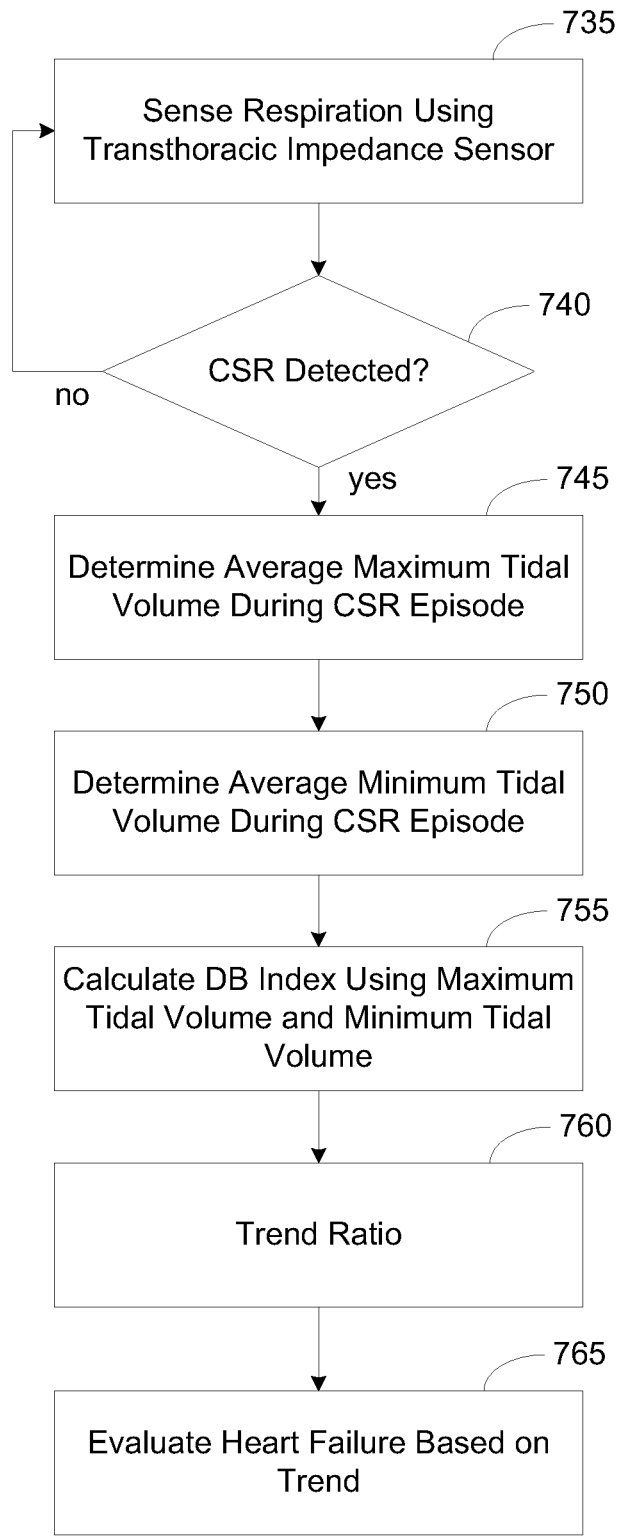
FIG. 7A is a flowchart of a method for evaluating heart failure status using a disordered breathing index determined based on modulation of tidal volume during Cheyne-Stokes respiration episodes in accordance with embodiments of the invention.

Worsening of HF symptoms may be associated with a corresponding increase in the depth of modulation of tidal volume during CSR. FIG. 7A illustrates an embodiment wherein the DB index is based on a degree or depth of modulation of tidal volume during CSR. In this exemplary embodiment, a transthoracic impedance sensor senses 735 respiration and generates a respiration signal. If a CSR episode is detected 740, then the average maximum tidal volume and average minimum tidal volume for the CSR episode are determined 745, 750. Alternatively, other measures of the tidal volume, e.g., highest TV (MaxTV) detected during hyperpnea phases and lowest TV (Min TV) detected during apneic phases of the CSR episode may be used instead of the average maximum and minimum values. In one example, the ratio of the average maximum TV to the average minimum TV may be calculated 755 as the DB index. In other examples, the modulation percentage 100(1−MinTV/MaxTV), or other DB index may be calculated. The DB index is trended 760 and HF evaluated 765 based on the trend.

Figure 7B:
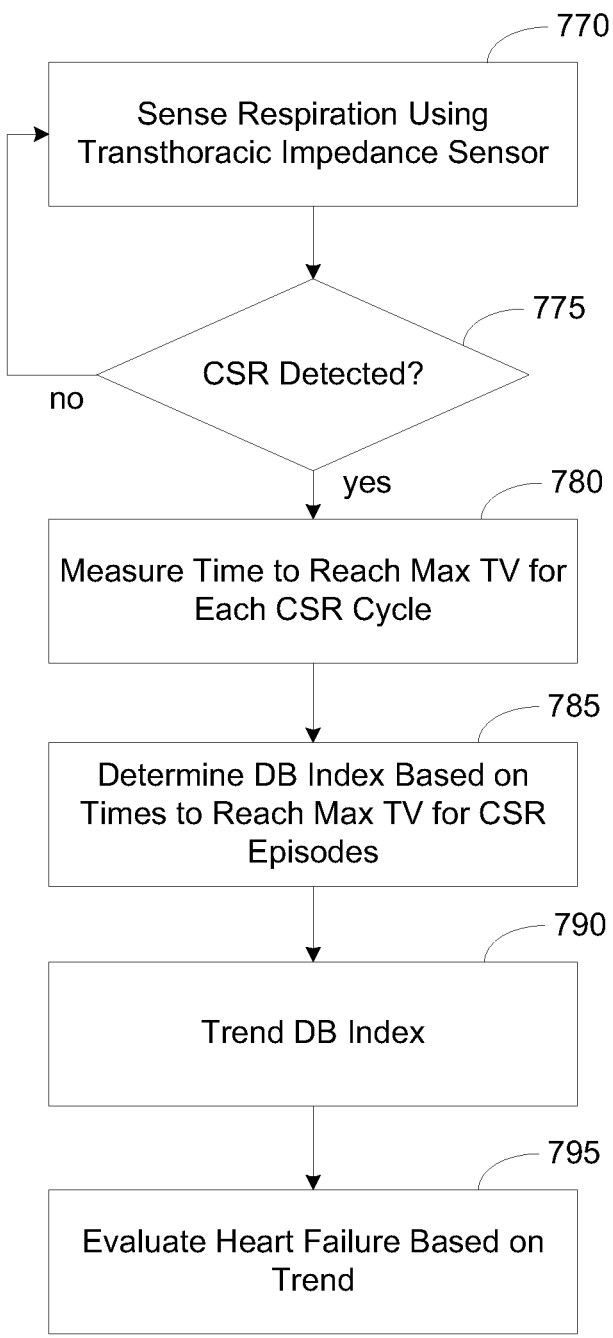
FIG. 7B is a flowchart of a method for evaluating heart failure status based on time to reach maximum tidal volume during Cheyne-Stokes respiration in accordance with embodiments of the invention.

FIG. 7B illustrates an embodiment wherein the DB index is based on the time it takes to achieve the maximum tidal volume during CSR. In this exemplary embodiment, a transthoracic impedance sensor senses 770 respiration and generates a respiration signal. If a CSR episode is detected 775, then the time to reach maximum tidal volume is measured 780 for each cycle of the CSR episode. The DB index is determined 785 based on a metric associated with the measured times to reach maximum tidal volume. For example, the DB index may be an average time, mean time, maximum or minimum time to reach maximum tidal volume for each episode. The DB index is trended 790 and HF evaluated 795 based on the trend.

Figure 8:
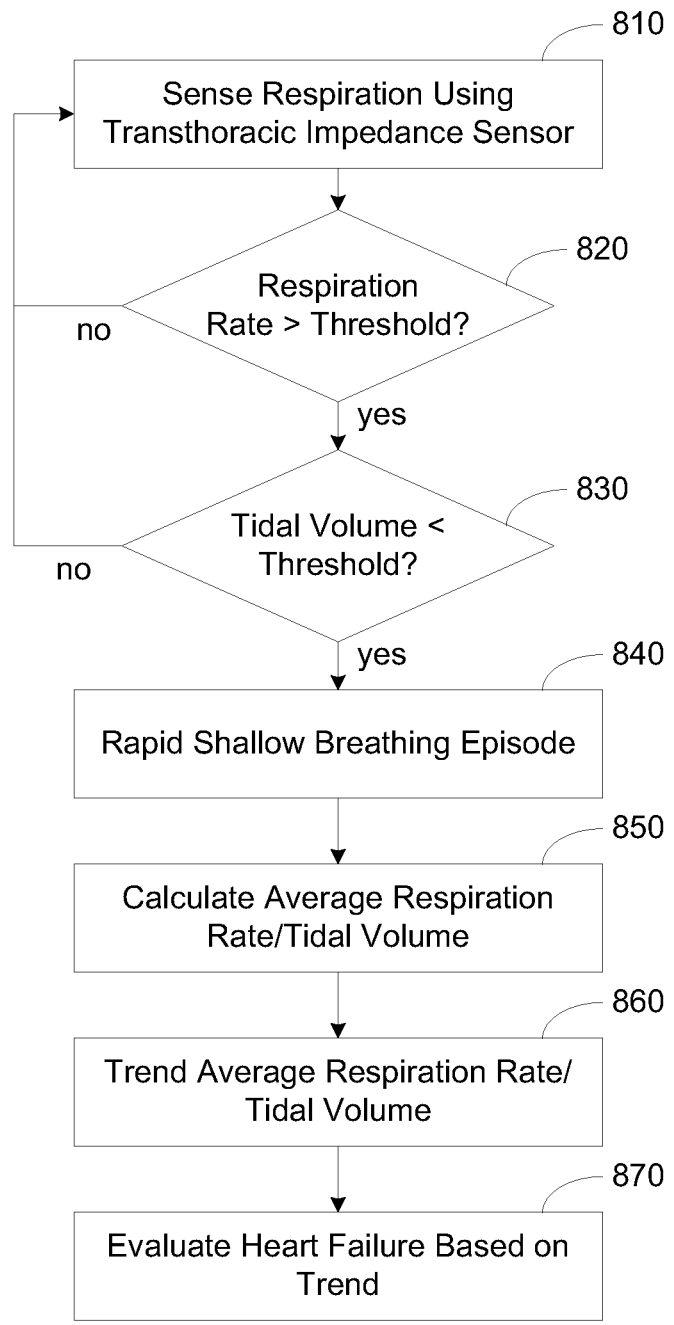
FIG. 8 is a flowchart of a method for evaluating heart failure status using a disordered breathing index determined based on a ratio of respiration rate to tidal volume during rapid shallow breathing episodes in accordance with embodiments of the invention.

Another useful index for tracking HF progression involves a rapid shallow breathing metric based on the relationship between the tidal volume and respiration rate during rapid shallow breathing episodes. The flowchart of FIG. 8 illustrates the use of a rapid shallow breathing metric. As before, the patient's respiration is sensed 810 via a transthoracic impedance sensor and a respiration signal is generated. If the patient's respiration rate is greater than 820 a threshold and the tidal volume of the respiration is below 830 a threshold, then the patient is experiencing 840 rapid shallow breathing. The ratio of the average respiration rate to the average tidal volume during the rapid shallow breathing is calculated 850 as the DB index. Alternatively other DB indices may be determined that are based on a relationship between respiration rate and tidal volume of rapid shallow breathing. A trend is developed 860 based on the DB index and the patient's HF status is evaluated 870 based on the trend.

In some embodiments, the DB index may be combined with other information or indices to develop a combination index that is used to evaluate HF status. For example, the combined index may be calculated based on a weighted average of the DB index and non-DB measurements, metrics, or indices derived from the additional information. In various embodiments, the DB index and the non-DB information may be combined via a weighted average, voting, data fusion, fuzzy logic, or other processes for combining data.

In some implementations, the additional information may used to inform or modify the DB index. For example, calculation of the DB index may take into account the context in which the DB episodes occur. For example, the DB index may be based on DB episodes that occur concurrently with certain postures of the patient, activity levels, a particular time of night, or particular sleep stages.

Figure 9:
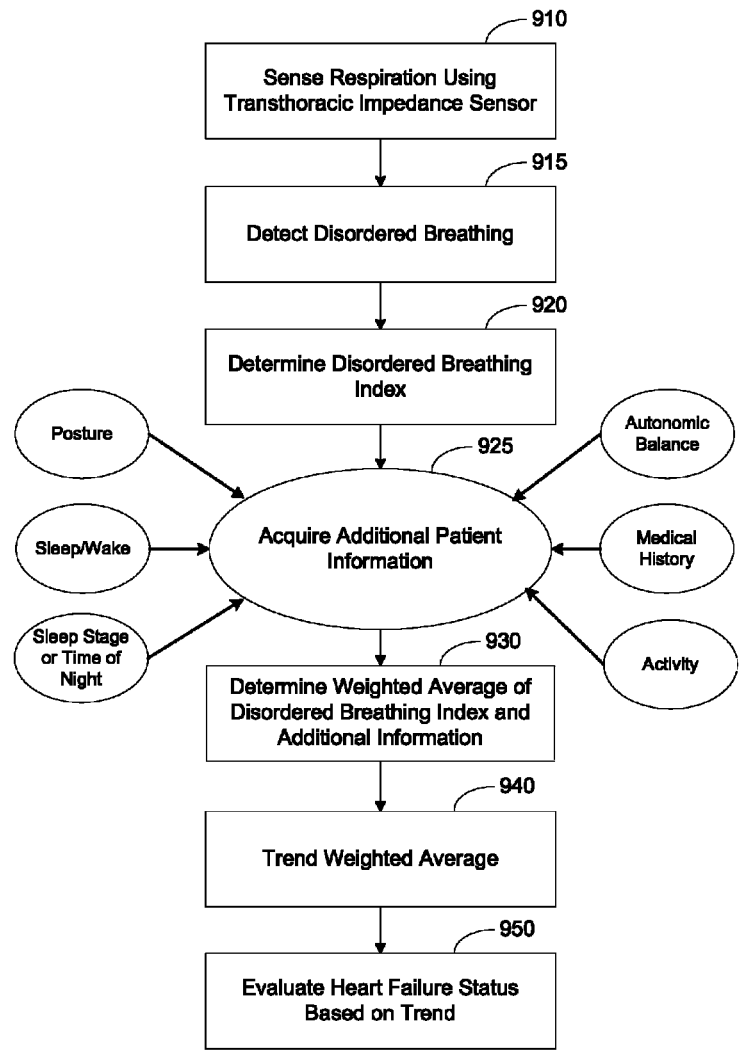
FIG. 9 is a flowchart of a method for evaluating heart failure status using a disordered breathing index combined with additional patient information in accordance with embodiments of the invention.

FIG. 9 is a flowchart illustrating one method of evaluating heart failure status based on a combined index. As previously described, disordered breathing is detected 915 based on sensed 910 patient respiration and a disordered breathing index is determined 920, for example, using any of the methods described herein. Additional patient information is acquired 925. A representative, non-limiting set of additional information is illustrated in FIG. 9. the additional information may include, for example, posture, sleep/wake cycles, autonomic balance, i.e., sympathetic nervous system (SNS) vs. parasympathetic nervous system (PNS) balance, cardiac functioning, medical history, patient activity, and/or other additional information. A combined index may be determined 930 based on a weighted average of the DB index and information from each of the additional information components. The combined index is trended 940 and used to evaluate 950 HF status.

Figure 10:
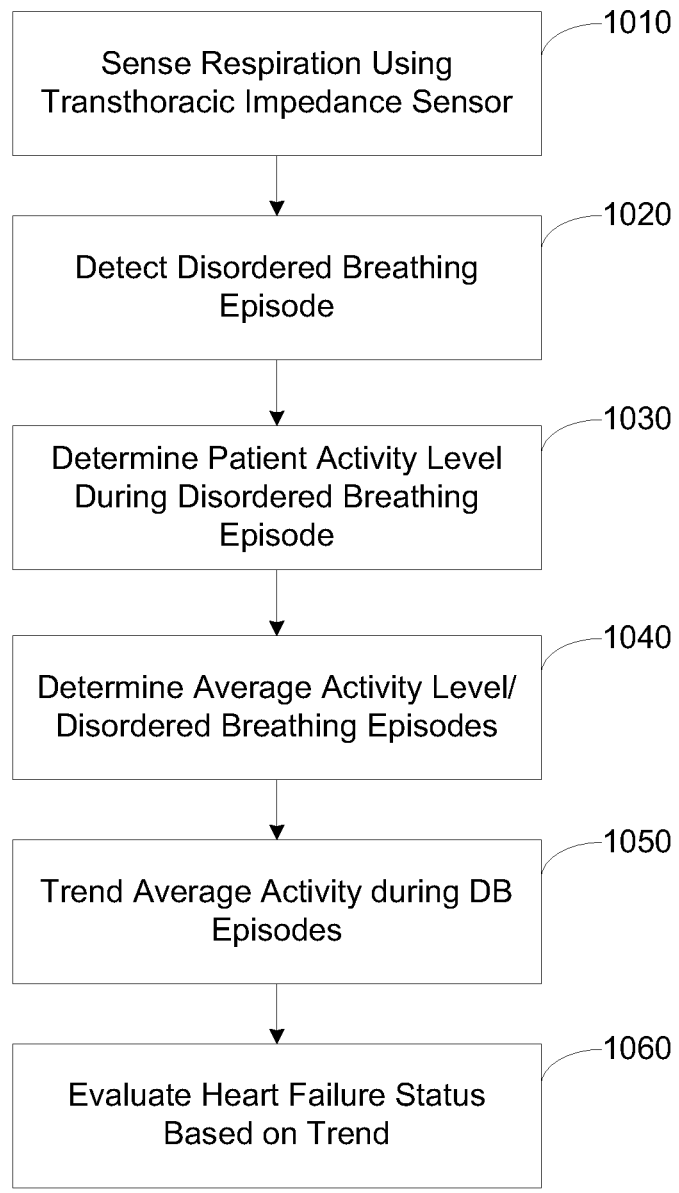
FIG. 10 is a flowchart of a method for evaluating heart failure status based on a disordered breathing index that takes into account patient activity during disordered breathing in accordance with embodiments of the invention.
Figure 11:
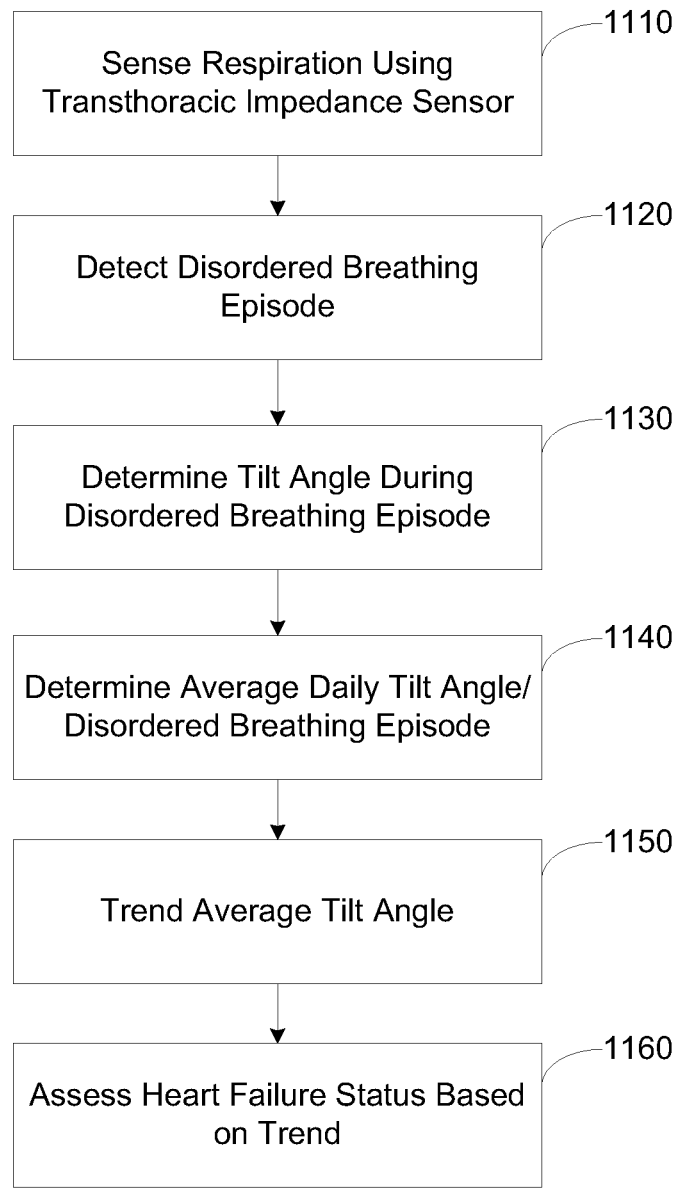
FIG. 11 is a flowchart of a method for evaluating heart failure status based on a disordered breathing index that takes into account patient posture during disordered breathing in accordance with embodiments of the invention.

FIGS. 10 and 11 illustrate methods for calculating modified DB indices that use the additional information to inform or modify the DB indices. The process illustrated in the flowchart of FIG. 10 uses patient activity to inform the DB index calculation. The process illustrated in the flowchart illustrated in FIG. 11 uses patient posture to inform the DB index calculation.

Turning now to FIG. 10, a process for using activity information to modify the DB index is illustrated. The exemplary embodiment is based on calculation of the average activity level of the patient during DB episodes. It will be appreciated that there are many ways activity level may be used to modify a DB index that are considered to be within the scope of the invention. The process illustrated in FIG. 10 provides one exemplary implementation for producing an activity informed DB index that may be used for HF status evaluation.

Patient respiration is sensed 1010 and a respiration signal is generated. Disordered breathing episodes are detected 1020 based on the respiration signal. The patient's activity level is determined 1030 during each disordered breathing episode. The average activity level during disordered breathing is determined 1040 for a period of time. The average activity level during DB is trended 1050 and HF status is evaluated 1060 based on the trend. For example, if the trend indicates that the patient activity during DB is generally decreasing, indicating an increase in DB during less active periods, this change may indicate a worsening of HF status.

FIG. 11 illustrates a process that uses patient posture information to modify the DB index is illustrated. The exemplary embodiment is based on calculation of the average tilt angle of the patient during DB episodes. It will be appreciated that there are many ways patient posture may be used to modify a DB index that are considered to be within the scope of the invention. The process illustrated in FIG. 11 provides one exemplary implementation for producing a posture informed DB index that may be used for HF status evaluation.

Patient respiration is sensed 1110 and a respiration signal is generated. Disordered breathing episodes are detected 1120 based on the respiration signal. The patient's tilt angle is determined 1130 during each disordered breathing episode. The average tilt angle during disordered breathing is determined 1140 over a period of time. The average tilt angle during DB is trended 1150 and HF status is evaluated 1160 based on the trend. For example, if the trend indicates that the patient tilt angle during DB is generally increasing, indicating an increase in DB episodes when standing or sitting upright, this change may indicate a worsening of HF status.

Various modifications and additions may be made to the embodiments discussed herein without departing from the scope of the present invention. Accordingly, the scope of the present invention should not be limited by the particular embodiments described above, but should be defined only by the claims set forth below and equivalents thereof.

What is claimed is:

1. A system for providing a patient assessment, the system comprising:
   a respiration sensor configured to generate a signal responsive to patient respiration; and
   a disordered breathing detector coupled to the respiration sensor and configured to detect disordered breathing episodes based on the respiration signal and discriminate between central disordered breathing episodes and obstructive disordered breathing episodes based on speed of transition to hyperventilation during the disordered breathing episodes; and an index processor configured to determine a ratio of the central disordered breathing episodes and the obstructive disordered breathing episodes and to determine a disordered breathing index using the ratio.

2. The system of claim 1, further comprising:

a trend processor configured to trend the disordered breathing index; and a diagnostics unit configured to evaluate heart failure status based on the trend.

3. The system of claim 1, further comprising a rapid eye movement (REM) detector, wherein the index processor is configured to correlate the disordered breathing episodes with REM and non-REM sleep stages.

4. The system of claim 1, further comprising a posture sensor configure to provide an output indicative of tilt angle during the disordered breathing episodes, wherein the index processor is configured to determine the disordered breathing index including weighing the disordered breathing episodes based on tilt angle.

5. The system of claim 1, further comprising an activity sensor configured to generate a patient activity signal, wherein the index processor is configured to determine the disordered breathing index using the activity signal including applying different weights to disordered breathing episodes that occur during periods of low activity and disordered breathing episodes that occur during periods of high activity.

6. The system of claim 1, wherein the disordered breathing detector is configured to discriminate between the central disordered breathing episodes and the obstructive disordered breathing episodes based on hyperventilation portions of the respiration signal during the disordered breathing episodes.

7. The system of claim 1, further comprising a pressure sensor configured to generate a pressure signal, wherein the disordered breathing detector is configured to further discriminate between the central disordered breathing episodes and the obstructive disordered breathing episodes based on the pressure signal.

8. The system of claim 7, wherein the pressure sensor is configured to sense intrathoracic pressure, intracardiac pressure or intravascular pressure.

* * * * *